(12) United States Patent
Escher

(10) Patent No.: US 12,133,886 B2
(45) Date of Patent: *Nov. 5, 2024

(54) METHOD FOR INDUCING A TOLEROGENIC IMMUNE RESPONSE

(71) Applicant: Loma Linda University, Loma Linda, CA (US)

(72) Inventor: Alan P. Escher, Loma Linda, CA (US)

(73) Assignee: Loma Linda University, Loma Linda, CA (US)

( * ) Notice: Subject to any disclaimer, the term of this patent is extended or adjusted under 35 U.S.C. 154(b) by 650 days.

This patent is subject to a terminal disclaimer.

(21) Appl. No.: 17/015,947

(22) Filed: Sep. 9, 2020

(65) Prior Publication Data

US 2021/0085771 A1 Mar. 25, 2021

Related U.S. Application Data

(63) Continuation of application No. 14/346,706, filed as application No. PCT/US2012/056761 on Sep. 21, 2012, now Pat. No. 10,813,987.

(60) Provisional application No. 61/538,682, filed on Sep. 23, 2011.

(51) Int. Cl.
| | |
|---|---|
| A61K 39/00 | (2006.01) |
| A61K 39/02 | (2006.01) |
| A61K 49/00 | (2006.01) |
| C12N 9/10 | (2006.01) |
| C12N 9/22 | (2006.01) |
| C12N 9/50 | (2006.01) |
| C12N 15/117 | (2010.01) |
| C12N 15/70 | (2006.01) |

(52) U.S. Cl.
CPC ...... *A61K 39/0241* (2013.01); *A61K 39/0008* (2013.01); *A61K 49/00* (2013.01); *C12N 9/1007* (2013.01); *C12N 9/22* (2013.01); *C12N 9/506* (2013.01); *C12N 15/117* (2013.01); *C12N 15/70* (2013.01); *C12N 2310/17* (2013.01)

(58) Field of Classification Search
CPC .................................................. A61K 39/0008
See application file for complete search history.

(56) References Cited

U.S. PATENT DOCUMENTS

| | | | |
|---|---|---|---|
| 6,410,273 B1 | 6/2002 | Crouzet et al. | |
| 9,358,277 B2 | 6/2016 | Li et al. | |
| 10,500,258 B2 | 12/2019 | Li et al. | |
| 10,813,987 B2 | 10/2020 | Escher | |
| 2002/0086332 A1 | 7/2002 | Mahan et al. | |
| 2003/0176378 A1 | 9/2003 | Weiner et al. | |
| 2006/0153842 A1 | 7/2006 | Lake et al. | |
| 2007/0082009 A1 | 4/2007 | Lawrence et al. | |
| 2008/0194510 A1 | 8/2008 | Escher et al. | |
| 2009/0191218 A1 | 7/2009 | Li et al. | |
| 2010/0068813 A1 | 3/2010 | Li et al. | |
| 2012/0308577 A1 | 12/2012 | Li et al. | |
| 2014/0288164 A1 | 9/2014 | Escher | |
| 2020/0316180 A1 | 10/2020 | Li et al. | |

FOREIGN PATENT DOCUMENTS

| | | |
|---|---|---|
| EP | 2 058 393 A1 | 5/2009 |
| WO | 99/44644 A1 | 9/1999 |
| WO | 00/59538 A2 | 10/2000 |
| WO | 01/32857 A1 | 5/2001 |
| WO | 2004/034966 A2 | 4/2004 |
| WO | 2006/114735 A1 | 11/2006 |
| WO | 2006/124375 A2 | 11/2006 |
| WO | 2008/058944 A1 | 5/2008 |
| WO | 2009/114735 A1 | 9/2009 |
| WO | 2010/030986 A2 | 3/2010 |
| WO | 2013/044177 A2 | 3/2013 |
| WO | 2014/145042 A1 | 9/2014 |

OTHER PUBLICATIONS

Liu, "DNA vaccines: a review," *Journal of Internal Medicine* 253:402-410, 2003.
Thomas et al., "Alopecia Areata and Autoimmunity: A Clinical Study," *Indian J. Dermatol.* 53(2):70-74, 2008 (10 pages).
Adams et al., "The Bcl-2 Protein Family: Arbiters of Cell Survival," *Science* 281:1322-1326, 1998.
Adamus et al., "Autoimmunity against Carbonic Anhydrase II Affects Retinal Cell Functions in Autoimmune Retinopathy," *J. Autoimmun.* 32(2): 133-139, 2009 (NIH Public Access Author Manuscript, available in PMC Mar. 1, 2010)(16 pages).
Andrés, "Cancer incidence after immunosuppressive treatment following kidney transplantation," *Critical Reviews in Oncology/Hematology* 56:71-85, 2005.
Balasa et al., "Vaccination with Glutamic Acid Decarboxylase Plasmid DNA Protects Mice from Spontaneous Autoimmune Diabetes and B7/CD28 Costimulation Circumvents That Protection," *Clinical Immunology* 99(2):241-252, 2001.
Bláková et al., "DNA vaccines: are they still just a powerful tool for the future?" *Arch. Immunol. Ther. Exp.* 55:387-398, 2007.
Björk et al., "Glucose Regulation of the Autoantigen $GAD_{65}$ in Human Pancreatic Islets," *Journal of Clinical Endocrinology and Metabolism* 75(6):1574-1576, 1992.
Borner et al., "The Protein bcl-2a Does Not Require Membrane Attachment, but Two Conserved Domains to Suppress Apoptosis," *The Journal of Cell Biology* 126:1059-1068, 1994.
Bros et al., "A newly established murine immature dendritic cell line can be differentiated into a mature state, but exerts tolerogenic function upon maturation in the presence of glucocorticoid," *Blood* 109(9):3820-3829, 2007.

(Continued)

*Primary Examiner* — Anoop K Singh
*Assistant Examiner* — David A Montanari
(74) *Attorney, Agent, or Firm* — Seed IP Law Group LLP

(57) ABSTRACT

The subject technology relates generally to compositions and methods for producing plasmid DNA of a desired quality. In addition, it relates to the discovery of *Escherichia coli* (*E. coli*) bacteria with a constitutive methylase gene stably incorporated into the chromosomal DNA and uses thereof.

18 Claims, 10 Drawing Sheets

Specification includes a Sequence Listing.

(56) References Cited

OTHER PUBLICATIONS

Bumgardner et al., "Unusual patterns of alloimmunity evoked by allogeneic liver parenchymal cells," *Immunological Reviews* 174:260-279, 2000.
Chao et al., "BCL-2 Family: Regulators of Cell Death," *Annu. Rev. Immunol.* 16:395-419, 1998.
Chaopatchayakul et al., "Aberrant DNA methylation of apoptotic signaling genes in patients responsive and nonresponsive to therapy for cervical carcinoma," *Am J Obstet Gynecol* 202:281 e1-e9, 2010.
Chattergoon et al., "Targeted antigen delivery to antigen-presenting cells, including dendritic cells by engineered Fas-mediated apoptosis," *Nature Biotechnology* 18:974-979, 2000.
Chernysheva et al., "T Cell Proliferation Induced by Autologous Non-T Cells is a Response to Apoptotic Cells Processed by Dendritic Cells," *J. Immunol.* 169(3):1241-1250, 2002 (11 pages).
Contreras et al., "Cytoprotection of pancreatic islets before and early after transplantation using gene therapy," *Kidney International* 61(Symposium 1):S79-S84, 2002.
Contreras et al., "Gene transfer of the Bcl-2 gene confers cytoprotection to isolated adult porcine pancreatic islets exposed to xenoreactive antibodies and complement," *Surgery* 130(2):166-174, 2001.
Delavallée et al., "Vaccination with cytokines in autoimmune diseases," *Annals of Medicine* 40:343-351, 2008.
Donnelly et al., "DNA Vaccines: Progress and Challenges," *J Immunol* 175:633-639, 2005 (8 pages).
Efrat et al., "Adenovirus Early Region 3 (E3) Immunomodulatory Genes Decrease the Incidence of Autoimmune Diabetes in NOD Mice," *Diabetes* 50:980-984, 2001.
Eisenberg, "Do autoantigens define autoimmunity or vice versa?" *Eur. J. Immunol.* 35:367-370, 2005.
Elnekave et al., "Intradermal naked plasmid DNA immunization: mechanisms of action," *Expert Rev. Vaccines* 10(8):1169-1182, 2011.
Erickson et al., "Expression of Carbonic Anhydrase II (CA II) Promoter-Reporter Fusion Genes in Multiple Tissues of Transgenic Mice Does Not Replicate Normal Patterns of Expression Indicating Complexity of CA II Regulation in Vivo," *Biochemical Genetics* 33(11/12):421-437, 1995.
Ferrera et al., "Gene Vaccination for the Induction of Immune Tolerance," *Ann. N.Y. Acad. Sci.* 1110:99-111, 2007.
Filippova et al., "Effects of Plasmid DNA Injection on Cyclophosphamide-Accelerated Diabetes in NOD Mice," *DNA and Cell Biology* 20(3):175-181, 2001.
Finetti et al., "The proapoptotic and antimitogenic protein p66SHC acts as a negative regulator of lymphocyte activation and autoimmunity," *Blood* 111(10):5017-5027, 2008.
Fletcher, "Development and validation of an approach to produce large-scale quantities of CpG-methylated plasmid DNA," *Microbial Biotechnology* 1(1):62-67, 2008.
Friedman et al., "Serum Cytokine Profiles Associated with Early Allograft Dysfunction in Patients Undergoing Liver Transplantation," *Liver Transplantation* 18(2):166-176, 2012.
García et al., "The Major Histocompatibility Complex in Transplantation," *Journal of Transplantation* 2012(842141): 1-7, 2012.
García-Sáez et al., "Peptides corresponding to helices 5 and 6 of Bax can independently form large lipid pores," *FEBS Journal* 273:971-981, 2006.
Gilhar et al., "Alopecia Areata: A tissue specific autoimmune disease of the hair follicle," *Autoimmunity Reviews* 5:64-69, 2006.
Guenette et al. "DNA methylation inhibits transcription of procollagen α2(I) promoters," *Biochem. J.* 283:699-703, 1992.
Gurumurthy et al., "Generating mouse models for biomedical research: technological advances," *Disease Models & Mechanisms* 12:1-10, 2019.
Hackam, "Translating animal research into clinical benefit," *BMJ* 334:163-164, 2007.
Harrison, "The Prospect of Vaccination to Prevent Type 1 Diabetes," *Human Vaccines* 1(4):143-150, 2005.

Hedstrand et al., "The Transcription Factors SOX9 and SOX10 are Vitiligo Autoantigens in Autoimmune Polyendocrine Syndrome Type I," *The Journal of Biological Chemistry* 276(38):35390-35395, 2001 (7 pages).
Horner et al., "Skin tolerance: in search of the Holy Grail," *European Society for Organ Transplantation* 21:101-112, 2008.
Hosoda et al., "Detection of autoantibody against carbonic anhydrase II in various liver diseases by enzyme-linked immunosorbent assay using appropriate conditions," *Clinica Chimica Acta* 342:71-81, 2004.
Huurman et al., "Cellular Islet Autoimmunity Associates with Clinical Outcome of Islet Cell Transplantation," *PLoS ONE* 3(6):e2435, 2008 (10 pages).
Igata et al., "Molecular cloning and functional analysis of the murine bax gene promoter," *Gene* 238:407-415, 1999.
Ilan et al., "Insertion of the adenoviral E3 region into a recombinant viral vector prevents antiviral humoral and cellular immune responses and permits long-term gene expression," *Proc. Natl. Acad. Sci. USA* 94:2587-2592, 1997.
Iwata et al., "Anti-Type V Collagen Humoral Immunity in Lung Transplant Primary Graft Dysfunction," *J Immunol* 181:5738-5747, 2008 (11 pages).
Justice et al., "Using the mouse to model human disease: increasing validity and reproducibility," *Disease Models & Mechanisms* 9:101-103, 2016.
Kagawa et al., "A binary adenoviral vector system for expressing high levels of the proapoptotic gene bax," *Gene Therapy* 7:75-79, 2000.
Kerkar et al., "Cytochrome P4502D6$_{193\text{-}212}$: A New Immunodominant Epitope and Target of Virus/Self Cross-Reactivity in Liver Kidney Microsomal Autoantibody Type 1-Positive Liver Disease," *J Immunol* 170:1481-1489, 2003 (10 pages).
Klinman et al., "Contribution of CpG Motifs to the Immunogenicity of DNA Vaccines," *The Journal of Immunology* 158:3635-3639, 1997 (6 pages).
Klinman et al., "Use of CpG oligodeoxynucleotides as immune adjuvants," *Immunological Reviews* 199:201-216, 2004.
Komura et al., "Repression of transient expression by DNA methylation in transcribed regions of reporter genes introduced into cultured human cells," *Biochimica et Biophysica Acta* 1260:73-78, 1995.
Krieg, "The role of CpG motifs in innate immunity," *Current Opinion in Immunology* 12:35-43, 2000.
Lalier et al., "Bax activation and mitochondrial insertion during apoptosis," *Apoptosis* 12:887-896, 2007.
Leuking et al., "Profiling of Alopecia Areata Autoantigens Based on Protein Microarray Technology," *Molecular & Cellular Proteomics* 4:1382-1390, 2005.
Li et al., "A therapeutic DNA vaccination strategy for autoimmunity and transplantation," *Vaccine* 28:1897-1904, 2010.
Li et al., "Co-delivery of pro-apoptotic BAX with a DNA vaccine recruits dendritic cells and promotes efficacy of autoimmune diabetes prevention in mice," *Vaccine* 22:1751-1763, 2004.
Li et al., "Decreased Insulitis and Blood Glucose Levels after Injection of GAD-Transduced Lymphocytes into NOD Mice," *Molecular Therapy* 6(6):701-709, 2002.
Li et al., "DNA Vaccination for Type 1 Diabetes Prolongs Skin Allograft Survival in a Donor-Specific Manner," *Clinical Immunology* 131:S76, 2009 (Abstract only).
Li et al., "DNA vaccines for transplantation," *Expert Opin. Biol. Ther.* 10(6):903-915, 2010.
Li et al., "Intradermal or Oral Delivery of GAD-Encoding Genetic Vaccines Suppresses Type 1 Diabetes," *DNA and Cell Biology* 22(4):227-232, 2003.
Li et al., "Pro-apoptotic DNA vaccination ameliorates new onset of autoimmune diabetes in NOD mice and induces foxp3+ regulatory T cells in vitro," *Vaccine* 24:5036-5046, 2006.
Lim et al., "Cutting Edge: Direct Suppression of B Cells by CD4+CD25+ Regulatory T Cells," *J Immunol* 175:4180-4183, 2005 (5 pages).
Martin et al., "Cell to Cell Interaction in the Immune Response," *Journal of Experimental Medicine* 128(4):855-874, 1968.
Mathisen et al., "Gene Therapy in Experimental Autoimmune Encephalomyelitis," *J. Clin. Immunol.* 20(5):327-333, 2000.

(56) References Cited

OTHER PUBLICATIONS

McCluskie et al., "Route and Method of Delivery of DNA Vaccine Influence Immune Responses in Mice and Non-Human Primates," *Molecular Medicine* 5(5):287-300, 1999.

McElwee et al., "Experimental Induction of Alopecia Areata-Like Hair Loss in C3H/HeJ Mice Using Full-Thickness Skin Grafts," *J Invest Dermatol* 111:797-803, 1998.

Mcgowan et al., "Characterization of the rat carbonic anhydrase II gene structure: sequence analysis of the 5' flanking region and 3' UTR," *Gene* 186: 181-188, 1997.

Meinck et al., "Antibodies against glutamic acid decarboxylase: prevalence in neurological diseases," *J Neurol Neurosurg Psychiatry* 71:100-103, 2001.

Miranda et al., "DNA Methylation: The Nuts and Bolts of Repression," *J. Cell. Physiol.* 213:384-390, 2007 (8 pages).

Nakao et al., "Regulation of transcription and chromatin by methyl-CpG binding protein MBD1," *Brain Development* 23:S174-6, 2001.

Nichol et al., "CpG Methylation Modifies the Genetic Stability of Cloned Repeat Sequences," *Genome Research* 12:1246-1256, 2002.

Ono et al., "Carbonic anhydrase in the membrane of the endoplasmic reticulum of male rat liver," *Proc. Natl. Acad. Sci. USA* 89:11721-11725, 1992.

Orkin et al., "Report and Recommendations of the Panel to Assess the NIH Investment in Research on Gene Therapy," Issued by the U.S. National Institute of Health, Bethesda, MD, 1995 (37 pages).

Pasquini et al., "The effect of CpG sequences on the B cell response to a viral glycoprotein encoded by a plasmid vector," *Gene Therapy* 6:1448-1455, 1999.

Peters et al., "The mouse as a model for human biology: a resource guide for complex trait analysis," *Nature Reviews* 8:58-69, 2007.

Pezzicoli et al., "Expression in T-cells of the proapoptotic protein p66SHC is controlled by promoter demethylation," *Biochemical and Biophysical Research Communications* 349:322-328, 2006.

Pierce et al., "Adenovirus Early Region 3 Antiapoptotic 10.4K, 14.5K, and 14.7K Genes Decrease the Incidence of Autoimmune Diabetes in NOD Mice," *Diabetes* 52:1119-1127, 2003.

Qu et al., "Demethylation and expression of methylated plasmid DNA stably transfected into HeLa cells," *Nucleic Acids Research* 27(11):2332-2338, 1999.

Rabinovitch et al., "Transfection of Human Pancreatic Islets With an Anti-Apoptotic Gene (bcl-2) Protects β-Cells From Cytokine-Induced Destruction," *Diabetes* 48:1223-1229, 1999.

Razin, "CpG methylation, chromatin structure and gene silencing—a three-way connection," *The EMBO Journal* 17(17):4905-4908, 1998.

Reindl et al., "Antibodies against the myelin oligodendrocyte glycoprotein and the myelin basic protein in multiple sclerosis and other neurological diseases: a comparative study," *Brain* 122:2047-2056, 1999.

Restifo, "Building better vaccines: how apoptotic cell death can induce inflammation and activate innate and adaptive immunity," *Curr. Opin. Immunol.* 12(5):597-603, 2000 (NIH Public Access Author Manuscript, available in PMC Aug. 29, 2007)(13 pages).

Reyes-Sandoval et al., "CpG Methylation of a Plasmid Vector Results in Extended Transgene Product Expression by Circumventing Induction of Immune Responses," *Molecular Therapy* 9(2):249-261, 2004.

Santos et al., "Drug discovery for alopecia: gone today, hair tomorrow," *Expert Opin Drug Discov.* 10(3):1-24, 2015.

Sasaki et al., "Adjuvant formulations and delivery systems for DNA vaccines," *Methods* 31:243-254, 2003.

Sasaki et al., "Apoptosis-mediated enhancement of DNA-raised immune responses by mutant caspases," *nature biotechnology* 19:543-547, 2001.

Scheerlinck, "Genetic adjuvants for DNA vaccines," *Vaccine* 19:2647-2656, 2001.

Scheule, "The role of CpG motifs in immunostimulation and gene therapy," *Advanced Drug Delivery Reviews* 44:119-134, 2000.

Schowalter et al., "Heterologous expression of adenovirus E3-gp19K in an Ela-deleted adenovirus vector inhibits MHC I expression in vitro, but does not prolong transgene expression in vivo," *Gene Therapy* 4:351-360, 1997.

Schudrowitz et al., "Growth Inhibition in Human Microendothelial Cells by Proinflammatory Cytokines and ProApoptotic Molecules Released from Peripheral Mononuclear Blood Cells in Alopecia Areata," *Journal of Investigative Dermatology Symposium Proceedings* 8(1):137, 2003 (Abstract No. 070).

Seetharam et al., "Alloimmunity and autoimmunity in chronic rejection," *Curr Opin Organ Transplant* 15(4):531-536, 2010 (NIH Public Access Author Manuscript, available in PMC Aug. 2, 20104)(9 pages).

Sellers, "Translating Mouse Models: Immune Variation and Efficacy Testing," *Toxicologic Pathology* 45(1):134-145, 2016.

Shabahang et al., "Recent Patents on Immunoregulatory DNA Vaccines for Autoimmune Diseases and Allograft Rejection," *Recent Patents on DNA & Gene Sequences* 4:122-131, 2010.

Sheikh et al., "Editorial: Gun, genes, and spleen: a coming of age for rational vaccine design," *Methods* 31:183-192, 2003.

Shu et al., "Gene Therapy for Autoimmune Disease," *Clinic Rev Allerg Immunol* 49:163-176, 2015.

Silva et al., "Surgical Methods for Full-Thickness Skin Grafts to Induce Alopecia Areata in C3H/HeJ Mice," *Comparative Medicine* 63(5):392-397, 2013.

Song et al., "Use of C57BL/6N mice on the variety of immunological researches," *Lab Anim Res* 33(2):119-123, 2017.

Steinman et al., "The Induction of Tolerance by Dendritic Cells That Have Captured Apoptotic Cells," *J. Exp. Med.* 191(3):411-416, 2000.

Sun et al., "The C3H/HeJ mouse and DEBR rat models for alopecia areata: review of preclinical drug screening approaches and results," *Experimental Dermatology* 17:793-805, 2008.

Szabó et al., "Structure and the Promoter Region of the Mouse Gene Encoding the 67-kD Form of Glutamic Acid Decarboxylase," *DNA and Cell Biology* 15(12):1081-1091, 1996.

Taniguchi et al., "High Prevalence of Autoantibodies Against Carbonic Anhydrase II and Lactoferrin in Type 1 Diabetes: Concept of Autoimmune Exocrinopathy and Endocrinopathy of the Pancreas," *Pancreas* 27(1): 26-30, 2003.

Thomas et al., "Progress and problems with the use of viral vectors for gene therapy," *Nature Reviews* 4:346-358, 2003.

Tisch et al. "Antigen-Specific Mediated Suppression of β Cell Autoimmunity by Plasmid DNA Vaccination," *J Immunol* 166:2122-2132, 2001 (12 pages).

Trucco et al., "Gene Therapy Strategies to Prevent Autoimmune Disorders," *Current Gene Therapy* 2:341-354, 2002.

Ulmer et al., "Gene-based vaccines: recent technical and clinical advances," *TRENDS in Molecular Medicine* 12(5):216-222, 2006.

Valero et al., "Bax-derived membrane-active peptides act as potent and direct inducers of apoptosis in cancer cells," *Journal of Cell Science* 124(4):556-564, 2010.

Valujskikh et al., "Development of Autoimmunity After Skin Graft Rejection Via an Indirect Alloresponse," *Transplantation* 73(7):1130-1137, 2002.

Wallet et al., "MerTK is required for apoptotic cell-induced T cell tolerance," *J. Exp. Med.* 205(1):219-232, 2008.

Watson et al., "'Pruning' of Alloreactive CD4+ T Cells Using 5-(and 6-)Carboxyfluorescein Diacetate Succinimidyl Ester Prolongs Skin Allograft Survival," *J Immunol* 173:6574-6582, 2004 (10 pages).

Weidner et al., "Defining the optimal animal model for translational research using gene set enrichment analysis," *EMBO Mol Med* 8(8):831-838, 2016.

Whisstock et al., "Prediction of protein function from protein sequence and structure," *Quarterly Reviews of Biophysics* 36(3):307-340, 2003.

Xavier-Elsas, "Ectopic lung transplantation induces the accumulation of eosinophil progenitors in the recipients' lungs through an allergen- and interleukin-5-dependent mechanism," *Clinical and Experimental Allergy* 37:29-38, 2007.

(56) References Cited

OTHER PUBLICATIONS

Yamaguchi et al., "The Effect of Pretreatment with Class I Major Histocompatibility Complex (MHC) Antigens on Hepatic or Cardiac Allograft Survival in the Rat," *Transplant Proc.* 21(3):3355, 1989.

Yi et al., "CpG Motifs in Bacterial DNA Activate Leukocytes Through the pH-Dependent Generation of Reactive Oxygen Species," *The Journal of Immunology* 160:4755-4761, 1998.

Yu et al., "Advances in transplantation tolerance," *The Lancet* 357:1959-1963, 2001.

Zardo et al., "Dynamic and reversibility of heterochromatic gene silencing in human disease," *Cell Research* 15(9):679-690, 2005.

METHOD FOR INDUCING A TOLEROGENIC IMMUNE RESPONSE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 110268_402C1_SEQUENCE_LISTING.txt. The text file is 6.3 KB, was created on Nov. 20, 2020, and is being submitted electronically via EFS-Web.

FIELD

The subject technology relates generally to compositions and methods for producing plasmid DNA of a desired quality. In addition, it relates to the engineering of *Escherichia coli* (*E. coli*) bacteria with a constitutively expressed methylase gene stably incorporated into the chromosomal DNA and uses thereof.

BACKGROUND

DNA methylation in vertebrates typically occurs at CpG sites. This methylation results in the conversion of the cytosine to 5-methylcytosine. The formation of Me-CpG is catalyzed by the enzyme DNA methyltransferase. Between 60% and 90% of all CpGs are methylated in mammals. Human DNA has about 80%-90% of CpG sites methylated.

Bacterial DNA contains low levels of methylated CpG dinucleotides compared to mammalian DNA. The mammalian immune system uses this feature of bacterial DNA as a signal to identify foreign DNA and respond to threats by bacterial pathogens.

SUMMARY

The subject technology relates to compositions and methods to construct strains of *E. coli* cells carrying a chromosomal copy of a toxic gene under the control of a constitutive promoter. In some non-limiting examples, the toxic gene may be a gene coding for the SssI methylase. *E. coli* containing the SssI methylase gene permit the cost-effective production of plasmid DNA for gene therapy with chosen increased percentage of methylated CpG dinucleotides depending on the choice of constitutive promoter, e.g., from 10% to 50% CpG methylation, for applications to DNA vaccination and gene therapy without contamination with a methylase-encoding plasmid DNA construct. The subject technology described below contains non-obvious steps that were used to overcome unforeseen difficulties in constructing the new strains.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 17. The other clauses can be presented in a similar manner.

1. An isolated bacterium with chromosomal DNA comprising an engineered methylase gene (or a polynucleotide encoding a methylase) controlled by a constitutive promoter stably incorporated into the chromosomal DNA.
2. The bacterium of clause 1, wherein the bacterium is *Escherichia coli* (*E. coli*).
3. The bacterium of clause 1 or 2, wherein the methylase gene is a CpG methylase gene.
4. The bacterium of clause 3, wherein the CpG methylase gene comprises an SssI gene.
5. The bacterium of clause 1 or 2, wherein the methylase gene comprises an M. CviPI gene, an M. AluI gene, an M BamHI gene, an M.dam gene, a Dnmt1 gene, an M EcoRI gene, an M HaeIII gene, an M. HhaI, an M.HpaII gene, an M. MspI gene, an M. TaqI gene, an M.G9a gene, an M. PRMT1 gene, or an M. SET7 gene.
6. An isolated bacterium with chromosomal DNA comprising an engineered toxic gene controlled by a constitutive promoter stably incorporated into the chromosomal DNA.
7. The bacterium of clause 6, wherein the bacterium is *Escherichia coli* (*E. coli*).
8. The bacterium of clause 6 or 7, wherein the engineered toxic gene comprises a DNaseI gene or a gene encoding an HIV-1 protease.
9. A method, for preparing a modified plasmid for use as a DNA vaccine or as a gene therapy agent, comprising expressing a plasmid encoding a protein of interest in a bacterium, wherein said bacterium has chromosomal DNA that comprises an engineered methylase gene (or a polynucleotide encoding a methylase) controlled by a constitutive promoter stably incorporated into the chromosomal DNA.
10. The method of clause 9, wherein the bacterium is *Escherichia coli* (*E. coli*).
11. The method of clause 9 or 10, wherein the protein of interest is: an allergen or an antigenic fragment thereof, an autoantigen or an antigenic fragment thereof, a cancer antigen or an antigenic fragment thereof, a donor antigen or an antigenic fragment thereof, a pro-apoptotic protein or a functional fragment thereof, or a combination thereof.
12. The method of clause 11, wherein the autoantigen is selected from the group consisting of carbonic anhydrase II, chromogranin, collagen, CYP2D6 (cytochrome P450, family 2, subfamily Device 400, polypeptide 6), glutamic acid decarboxylase, secreted glutamic acid decarboxylase 55, hCDR1, HSP60, IA2, IGRP, insulin, myelin basic protein, hNinein, Ro 60 kDa, SOX-10 (SRY-box containing gene 10), ZnT8, and an antigenic fragment thereof.
13. The method of clause 11, wherein the allergen is selected from the group consisting of peanut allergens Ara h 1, 2 and 3; pollen allergens Phl p 1, 2, 5a, 5b, 6, and Bet v 1; cat allergen Fel d 1; and an antigenic fragment thereof.
14. The method of clause 11, wherein the donor antigens comprise at least one of a major or a minor histocompatibility complex molecule.
15. The method of clause 11, wherein the cancer antigen is selected from the group consisting of HER-2, gp100, melan A, PSA, and an antigenic fragment thereof.
16. The method of clause 11, wherein the pro-apoptotic protein is selected from the group consisting of BAK, BAX, BIM, a modified caspase, Death Receptor 3 (DR3), Death Receptor 4 (DR4), Death Receptor 5

(DR5), a FAS receptor, a modified survivin protein, a Tumor Necrosis Factor Receptor, and a functional fragment thereof.

17. A method, for increasing the expression of regulatory T cells (Tregs) in a mammal, comprising contacting the mammal with a modified plasmid generated in a bacterium having chromosomal DNA comprising an engineered methylase gene controlled by a constitutive promoter stably incorporated into the chromosomal DNA.

18. The method of clause 17, wherein the bacterium is *Escherichia coli* (*E. coli*).

19. The method of clause 17 or 18, wherein the modified plasmid encodes an allergen, an autoantigen, a donor antigen, or a pro-apoptotic protein.

20. The method of clause 19, wherein the autoantigen is selected from the group consisting of carbonic anhydrase II, chromogranin, collagen, CYP2D6 (cytochrome P450, family 2, subfamily Device 400, polypeptide 6), glutamic acid decarboxylase, secreted glutamic acid decarboxylase 55, hCDR1, hNinein, HSP60, IA2, IGRP, insulin, myelin basic protein, Ro 60 kDa, SOX-10 (SRY-box containing gene 10), ZnT8, and an antigenic fragment thereof.

21. The method of clause 19, wherein the pro-apoptotic protein is selected from the group consisting of BAK, BAX, BIM, a modified caspase, Death Receptor 3 (DR3), Death Receptor 4 (DR4), Death Receptor 5 (DR5), a FAS receptor, modified surviving protein, Tumor Necrosis Factor Receptor, and a functional fragment thereof.

22. A kit, for preparing a modified plasmid for use as a DNA vaccine or a recombinant gene therapy agent, comprising:
    (a) a bacterium with a chromosomal DNA comprising an engineered methylase gene controlled by a constitutive promoter stably incorporated into the chromosomal DNA; and
    (b) instructions for use in expressing a plasmid encoding a gene of interest.

23. The bacterium of clause 22, wherein the bacterium comprises *Escherichia coli* (*E. coli*).

24. A method for incorporating a gene toxic to an *Escherichia coli* (*E. coli*) bacteria, the gene controlled by a constitutive promoter, the method comprising (a) selecting a plasmid containing the gene and a selectable marker in a proper orientation; (b) amplifying the plasmid in vitro to produce a microgram quantity of the plasmid; (c) electroporating the plasmid into the *E. coli*; and (d) selecting the *E. coli* incorporating the gene.

25. The method of clause 24, wherein the amplifying is performed by a rolling circle amplification.

26. The method of clause 24 or 25, wherein the gene toxic to *E. coli* comprises a methylase gene.

27. A method for treating an autoimmune disease, comprising administering to a subject in need thereof a therapeutically effective amount of: (a) a first polynucleotide comprising a sequence that encodes an autoantigen, or an antigenic fragment thereof, wherein at least about 50% of the CpG dinucleotides of said first polynucleotide are methylated; and (b) a second polynucleotide comprising a sequence that encodes a pro-apoptotic protein, or a functional fragment thereof; wherein about 15%, or less, of the CpG dinucleotides of said second polynucleotide are methylated.

28. The method of clause 27, wherein said first polynucleotide and second polynucleotide are administered at a ratio of from about 4:1 to about 4:2 (µg:µg).

29. A method for treating an autoimmune disease, comprising administering to a subject in need thereof a therapeutically effective amount of: (a) a first polynucleotide comprising a sequence that encodes an autoantigen, or an antigenic fragment thereof; and (b) a second polynucleotide comprising a sequence that encodes a pro-apoptotic protein, or a functional fragment thereof, wherein from about 40% to about 45% of the CpG dinucleotides of said first and second polynucleotide are methylated.

30. The method of any one of clauses 27-29, wherein said autoimmune disease comprises Type I diabetes.

31. The method of any one of clauses 27-30, wherein said autoantigen is glutamic acid decarboxylase (GAD), a secreted form of GAD (sGAD), or an auto-antigenic fragment thereof.

32. The method of any one of clauses 27-31, wherein said pro-apoptotic protein is BAX, or a functional fragment thereof.

33. A method for treating a transplant recipient, comprising administering to a subject in need thereof a therapeutically effective amount of: (a) a first polynucleotide comprising a sequence that encodes donor antigen, or an antigenic fragment thereof, wherein at least about 50% of the CpG dinucleotides of said first polynucleotide are methylated; and (b) a second polynucleotide comprising a sequence that encodes a pro-apoptotic protein, or a functional fragment thereof; wherein about 15%, or less, of the CpG dinucleotides of said second polynucleotide are methylated.

34. The method of clause 33, wherein said transplant comprises skin transplant.

35. A method of adjusting methylation level of a DNA plasmid for treating an autoimmune disease, wherein said DNA plasmid encodes an autoantigen or an antigenic fragment thereof, and is produced by a bacterium of clause 1, comprising:
    (i) administering said DNA plasmid to a subject in need thereof;
    (ii) determining a therapeutic effect of said DNA plasmid; and
    (iii) adjusting a methylation level of said DNA based on the therapeutic effect.

36. A method of adjusting methylation level of a DNA plasmid for treating a transplant recipient, wherein said DNA plasmid encodes a donor antigen or an antigenic fragment thereof, and is produced by a bacterium of clause 1, comprising:
    (i) administering said DNA plasmid to a subject in need thereof;
    (ii) determining a therapeutic effect of said DNA plasmid; and
    (iii) adjusting a methylation level of said DNA based on the therapeutic effect.

37. A method of adjusting methylation level of a DNA plasmid for gene therapy, wherein said DNA plasmid encodes a therapeutic protein and is operably linked to a promoter, and is produced by a bacterium of clause 1, comprising:
    (i) administering said DNA plasmid to a subject in need thereof;
    (ii) determining a therapeutic effect of said DNA plasmid; and (iii) adjusting a methylation level of said DNA based on the therapeutic effect.

38. A method of expressing a protein of interest in a target cell or target tissue of a subject, comprising: administering a plasmid DNA to a subject in need thereof, wherein said plasmid DNA comprises a polynucleotide that encodes a therapeutic protein, and is operably linked to a promoter, wherein said promoter can be activated in the target cell or target tissue, and wherein said DNA plasmid is produced by the bacterium of clause 1.

39. A method of providing a DNA plasmid for expressing a protein of interest in a target cell or target tissue of a subject, comprising:
   (i) selecting a promoter that can be activated in the target cell or target tissue;
   (ii) determining a methylation level for said promoter, such that a transcriptional repression of the promoter by methylation is no more than 50%;
   (iii) operably linking said promoter to a polynucleotide sequence encoding said protein of interest to create a DNA plasmid;
   (iv) producing said DNA plasmid using a bacterium of clause 1 according to the methylation level determined in step (ii).

These and other embodiments of the subject technology are described in more detail herein below, which are to be regarded as illustrative, and non-limiting.

BRIEF DESCRIPTION OF THE FIGURES

FIG. 3 shows that increased DNA methylation causes decreased infiltration of islets by CD8*+ T lymphocytes. CpG-methylation causes an antigen-dependent increase in percentage of CD4+CD25+Foxp3+ in vitro. *, P<0.05.

DETAILED DESCRIPTION

1. Overview

Figure 1:
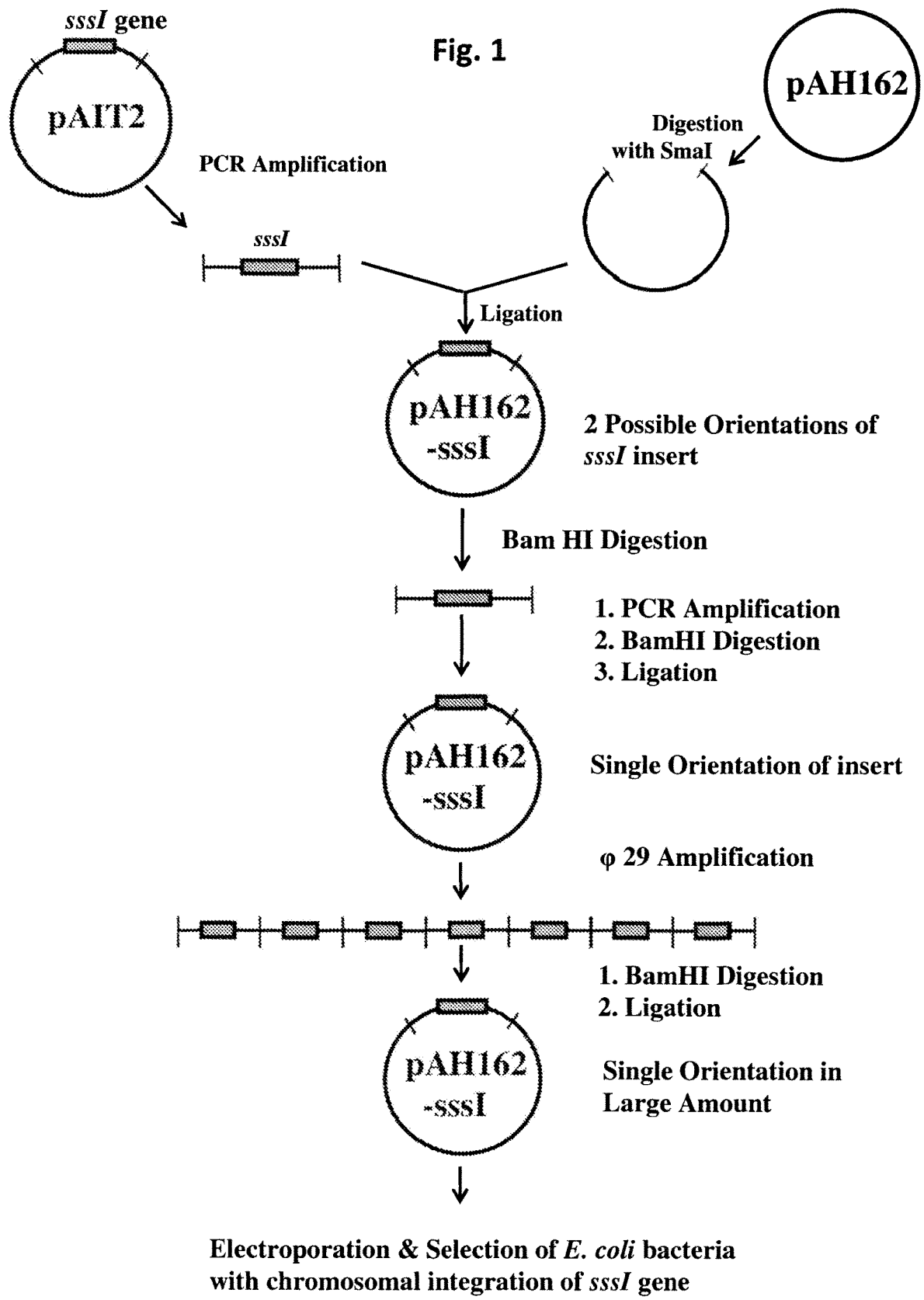
FIG. 1 is a schematic illustration of chromosomal integration of the sssI gene into E. coli.

Bacterial DNA contains low levels of methylated CpG dinucleotides compared to mammalian DNA. The mammalian immune system uses this feature of bacterial DNA as a signal to identify foreign DNA and respond to threats by bacterial pathogens. Accordingly, unmethylated CpG dinucleotides can serve as adjuvant for DNA vaccines engineered to induce effector responses against pathogens. In contrast, unmethylated CpG dinucleotides are detrimental for plasmid DNA vaccines engineered to induce an immunoregulatory response to suppress and control inflammation in disorders like autoimmune disease, allergy, asthma, organ transplant rejection, and cancer. Moreover, presence of unmethylated CpG dinucleotides in plasmid DNA also shortens time of gene expression in animals, which can be detrimental to gene therapy approaches. Accordingly, methylation of CpG dinucleotides could be used to enhance the potency of DNA vaccines for immune-mediated inflammatory disorders, to increase the time of therapeutic gene expression for gene therapy, and to enable multiple dosing without an immune-based adverse reaction.

Currently, it is possible to generate CpG-methylated plasmid DNA after amplification in bacterial strains carrying plasmid DNA encoding an enzyme like the SssI methylase, or to use the purified enzymes to methylate plasmid DNA in vitro. However, in vitro plasmid methylation cannot be envisaged for the industrial production of a plasmid which would be used in gene therapy. A method of plasmid DNA production must, in effect, enable large and homogeneous amounts of plasmids to be produced reproducibly, cost effectively, and this DNA to be purified by methods which are acceptable for pharmaceutical application.

Similarly, amplification of hypermethylated plasmid DNA in bacteria using a plasmid DNA construct encoding the methylase of interest cannot be readily translated to human therapeutics because of contamination with the methylase-encoding plasmid DNA, and the possibility of inconsistent methylation of the DNA produced resulting from variation in the copy number of the methylase-encoding plasmid DNA. The use of a plasmid DNA or expression cassette containing a gene encoding methylase M. SssI in bacterial cells under the control of an IPTG inducible promoter, where greater than 90% of the cytosines are methylated, is currently possible.

The incorporation of the SssI methylase gene into the E. coli chromosome under the control of an inducible promoter (arabinose-inducible promoter, PBAD), where greater than 90% of CpG sites are methylated, is also currently possible. However, over-methylation can lead to production of plasmid DNA that is not optimal for gene therapy or immune stimulation, as will be shown in the present disclosure. Accordingly, above described inducible system is inappropriate to make consistent plasmid products with intermediate methylation, e.g., 30-50%. Moreover, the inducible system introduces additional variables that create uncertainty in the reproducible production of methylated DNA plasmid DNA for commercial gene therapy applications. For example, the timing of induction for a specific batch could significantly impact levels of plasmid DNA methylation.

Alternatively, CpG dinucleotides present in plasmid DNA can be replaced with other nucleotides for human application but this requires time-consuming genetic engineering and trial and error testing. In addition, the promoter sequence and the sequence of the gene of interest may not function optimally after genetic engineering to remove the CpG dinucleotides. Thus, the replacement of CpG methodology is not readily applicable to any plasmid DNA construct of choice. Lastly, for human gene therapy applications, the modified promoter sequence and modified gene of interest raise additional issues and uncertainty with regard to safety and efficacy.

The construction of E. coli strains carrying chromosomal copies of a CpG-methylase gene under control of a constitutive promoter circumvents these problems and is described in detail herein.

Further, different levels of DNA methylation (e.g., about 50% CpG methylation, about 40% CpG methylation, about 30% CpG methylation, about 25% CpG methylation, etc.) may be desired for different applications. Levels of methylation can be adjusted by multiple methods, such as by modulating the expression level of methylase in the bacterial host (for example, by using promoters of different strength).

In another aspect, as described and exemplified herein, the inventors discovered that superior results were achieved by mixing hypomethylated plasmid DNA (e.g., around 10-15% CpG methylation, or lower) encoding pro-apoptotic protein (BAX), and hypermethylated plasmid DNA (e.g., 50% CpG methylation) encoding an antigen, to induce immune tolerance to said antigen. The antigen may be encoded by a plasmid DNA as exemplified herein, or it may be co-injected with a plasmid DNA, or present at the site of injection of a plasmid DNA, provided that it is present or synthesized in sufficient amounts. Data presented herein demonstrate that a mixture of hypomethylated and hypermethylated plasmid DNAs achieved higher efficacy, as compared to hypomethylated or hypermethylated plasmid DNA alone, in treating type 1 diabetes (T1D) in non-obese diabetic (NOD) mice. Accordingly, hypomethylated and hypermethylated DNA may be mixed to achieve a desired methylation level for a specific therapeutic application.

In another aspect, the subject technology provides an isolated bacterium with chromosomal DNA comprising a toxic engineered gene controlled by a constitutive promoter stably incorporated into the chromosomal DNA. In various embodiments, the bacterium comprises E. coli. In various embodiments, the toxic engineered gene of the E. coli bacteria described herein comprises a DNaseI gene or a gene encoding an HIV-1 protease.

As described and exemplified herein, the inventors discovered that when the methylase gene sssI was introduced into an E. coli cell in the form of a plasmid, such that the plasmid was replicated in vivo, the methylase gene became toxic to the bacterial host. It is believed that when the plasmid was replicated in vivo, methylase was expressed at a dose that caused toxicity, killing the host cells before the plasmid could be integrated into the genome. Accordingly, the inventors replicated the plasmid in vitro, such that enough copies of sssI genes were directly introduced into the host cell without the need for in vivo replication. By this way, the sssI gene was integrated into the genome without the requirement of in vivo replication. Because of the low copy number of genome-integrated sssI gene (as compared to a copy number plasmid), the amount of methylase produced this way did not reach the toxic level. This method can be used to recombinantly express other genes that are toxic to the host.

Accordingly, some methods of the subject technology further include incorporating a gene toxic to an *Escherichia* coli (*E. coli*) bacteria controlled by a constitutive promoter, the method comprising (a) selecting a plasmid containing the gene toxic to *E. coli* and a selectable marker in the proper orientation; (b) amplifying the plasmid in vitro to produce a microgram quantity of the plasmid; (c) electroporating the plasmid into the *E. coli*; and (d) selecting the *E. coli* incorporating the gene toxic to the *E. coli*. Some methods provide that the amplifying is performed by a rolling circle amplification. Some methods provide that the gene toxic to *E. coli* comprises a methylase gene.

While the subject technology is capable of being embodied in various forms, the description below of several embodiments is made with the understanding that the present disclosure is to be considered as an exemplification of the subject technology, and is not intended to limit the subject technology to the specific embodiments illustrated. Headings are provided for convenience only and are not to be construed to limit the subject technology in any manner. Embodiments illustrated under any heading may be combined with embodiments illustrated under any other heading.

2. Definitions

The use of numerical values in the various ranges specified in this application, unless expressly indicated otherwise, are stated as approximations as though the minimum and maximum values within the stated ranges were both preceded by the word "about." Slight variations above and below the stated ranges may be used to achieve substantially the same results as values within the ranges. The disclosure of ranges is intended as a continuous range including every value between the minimum and maximum values recited as well as any ranges that can be formed by such values. Accordingly, the skilled person will appreciate that many such ratios, ranges, and ranges of ratios can be unambiguously derived from the data and numbers presented herein and all represent various embodiments of the subject technology.

As used in this disclosure, the term "comprise" and variations of the term, such as "comprising" and "comprises," are not intended to exclude other additives, components, integers, or steps.

As used in this disclosure, the term "constitutive promoter" means and includes promoters that express a gene whether or not an inducer is present.

As used in this disclosure, the term "autoantigen" means and includes an endogenous antigen that stimulates the production of autoantibodies, as in an autoimmune reaction, as well as part of such endogenous antigens, or modified endogenous antigens that elicit the same response as the full endogenous antigen, as will be understood by those with skill in the art with reference to this disclosure. For example, in the context of this disclosure carbonic anhydrase II, chromogranin, collagen, CYP2D6 (cytochrome P450, family 2, subfamily Device 400, polypeptide 6), glutamic acid decarboxylase, secreted glutamic acid decarboxylase 55, hCDR1, HSP60, IA2, IGRP, insulin, myelin basic protein, hNinein, Ro 60 kDa, SOX-10 (SRY-box containing gene 10), ZnT8, and the like, are autoantigens. Also encompassed are antigenic fragments of the any one of the foregoing autoantigens.

As used in this disclosure, the term "donor antigen" means and includes an antigen from an allograft that was transplanted into the organism to take the place of defective or absent cells or tissues, such as for example, islet cell transplants, and partial or whole organ transplants including transplanted hearts, lungs, kidneys and livers, and that stimulates the production of antibodies and leukocytes that produce an immune reaction, as well as part of such donor antigens, or modified donor antigens that elicit the same response as the full donor antigen, as will be understood by those with skill in the art with reference to this disclosure. Also encompassed are antigenic fragments of the any one of the foregoing donor antigens.

As used in this disclosure, the term "immune-mediated inflammatory disorders" means and includes both diseases due in part or in total to destruction of normal cells or tissues by the immune system of the organism, and also comprises destruction by the immune system of the organism of cells or tissues (allografts) that were transplanted into the organism to take the place of defective or absent cells or tissues, such as for example, islet cell transplants, and partial or whole organ transplants including transplanted hearts, lungs, kidneys and livers. The immune-mediated inflammatory disorder may be, for example, the rejection of solid organ transplants, graft versus host disease, host versus graft disease, autoimmune hepatitis, vitiligo, diabetes mellitus type 1, Addison's Disease, Graves' disease, Hashimoto's thyroiditis, multiple sclerosis, polymyalgia rheumatica, Reiter's syndrome, Crohn's disease, Goodpasture's syndrome, Gullain-Barre syndrome, lupus nephritis, rheumatoid arthritis, systemic lupus erythematosus, Wegener's granulomatosis, celiac disease, dermatomyositis, eosinophilic fasciitis, idiopathic thrombocytopenic purpura, Miller-Fisher syndrome, myasthenia gravis, pemphigus vulgaris, pernicious anaemia, polymyositis, primary biliary cirrhosis, psoriasis, psoriatic arthritis, rheumatoid arthritis, Sjögren's syndrome, and the like.

As used in this disclosure, the term "DNA vaccine" means and includes DNA sequences that code for immunogenic proteins located in appropriately constructed plasmids, which include strong promoters, which when injected into an animal are taken up by cells and the immunogenic proteins are expressed and elicit an immune response.

As used in this disclosure, the term "gene therapy" means and includes correcting or ameliorating a deficiency or an abnormality by introducing genetic information into either an affected cell or organ, or into a non-affected cell or organ, so as to correct or ameliorate the deficiency and abnormality as a result of the gene therapy. This information may be introduced either in vitro into cells extracted from the organ or other cells such as a stem cell, and then re-injecting the modified into the body, ex vivo by introduction to a removed tissue or organ; or in vivo, directly into the target tissue.

The term "about", as used here, refers to +/−5% of a value.

The term "functional fragment" of protein refers to refers to a peptide fragment that is a portion of the full length protein, and has substantially the same biological activity, or carries out substantially the same function as the full length protein (e.g., carrying out the same enzymatic reaction). For example, a functional fragment of a pro-apoptotic protein can promote the apoptosis of a cell.

The term "hypermethylated" (sometimes abbreviated as "methylated") when used in reference to a DNA, means that at least about 30% (preferably at least about 35%, or at least about 40%, or at least about 45%, at least about 50%, at least about 55%, at least about 60%, at least about 65%, at least about 70%) of the CpG dinucleotides are methylated. For example, mammalian DNA, in which between 60% and 90% of all CpGs are methylated, is hypermethylated.

The term "hypomethylated" (sometimes abbreviated as "unmethylated") when used in reference to a DNA, means that about 15% or less (preferably about 10% or less, about 7.5% or less, about 5% or less, or about 3%, or about 1% or less) of the CpG dinucleotides are methylated. For example, bacterial DNA, in which between 5% and 15% of all CpGs are methylated, is hypomethylated.

A "methylation" level, when used in reference to a DNA, refers to the percentage of methylated CpG dinucleotides out of the total CpG dinucleotides of the DNA molecule.

The term "controlled" means "operably linked," which refers to the association of a nucleic acid sequence on another nucleic acid fragment so that the function of one is affected by the other. For example, a coding sequence is "controlled" by a promoter when the promoter is capable of affecting the expression of that coding sequence (i.e., that the coding sequence is under the transcriptional control of the promoter). Coding sequences can be operably linked to regulatory sequences in sense or antisense orientation.

3. Bacterial Strains Expressing Methylase

In one aspect, the subject technology provides an isolated bacterium comprising an engineered polynucleotide sequence encoding a methylase controlled by a constitutive promoter, wherein said engineered polynucleotide is stably incorporated into the chromosomal DNA of said bacterium.

Suitable bacteria include, e.g., *Bacillus brevis, Bacillus megaterium, Bacillus subtilis, Caulobacter crescentus*, other strains, or, *Escherichia coli*. In certain embodiments, the bacterium is *E. coli*.

A. Methylase and Nucleic Acid Encoding a Methylase

Methylase, also known as methyltransferase (MTase), is a type of transferase enzyme that transfers a methyl group from a donor to an acceptor. All the known DNA methyltransferases use S-adenosyl methionine (SAM) as the methyl donor.

MTases can be divided into three different groups on the basis of the chemical reactions they catalyze: 6A—those that generate N6-methyladenine (EC 2.1.1.72); m4C—those that generate N4-methylcytosine (EC 2.1.1.113); and m5C—those that generate C5-methylcytosine (EC 2.1.1.37). m6A and m4C methyltransferases are found primarily in prokaryotes. m5C methyltransfereases are found in some lower eukaryotes, in most higher plants, and in animals beginning with the echinoderms.

Nucleic acid sequences encoding various MTase have been found in many published genome sequences. See e.g., REBASE database (http://rebase.neb.com/rebase); or GenBank database (http://www.ncbi.nlm.nih.gov/genbank).

In one embodiment, the subject technology provides an isolated bacterium with chromosomal DNA comprising an engineered methylase gene controlled by a constitutive promoter stably incorporated into the chromosomal DNA. In various embodiments, the bacterium comprises *E. coli*. In various embodiments, the methylase gene of the *E. coli* bacteria described herein comprises a CpG methylase gene, M. CviPI gene, an M. AluI gene, an M BamHI gene, an M.dam gene, a DnmtI gene, an M. EcoRI gene, an M. HaeIII gene, an M HhaI, an MHpaII gene, an M. MspI gene, an M. TaqI gene, an M.G9a gene, an M PRMT1 gene, or an M. SET7 gene. In some embodiments, the CpG methylase gene comprises an SssI gene. A methylase gene encompasses genomic form, cDNA form, or variants of genomic form or cDNA form (e.g., mutants or fragments) of a nucleic acid that encodes a methylase.

B. Expression Level of Methylase

As described herein, different levels of DNA methylation (e.g., about 50% CpG methylation, about 45% CpG methylation, about 40% CpG methylation, about 35% CpG methylation, about 30% CpG methylation, about 25% CpG methylation, about 20% CpG methylation, about 15% CpG methylation, etc.) may be desired for different applications. In one aspect, levels of methylation can be adjusted by modulating the expression level of a methylase in the bacterial host. For example, if high level of DNA methylation is desired, a strong promoter may be used to increase the expression level of methylase.

Expression level of a methylase in the bacterial host can be modulated several ways. The transcriptional promoter and terminator sequences, the ribosome-binding site (RBS) and the efficiency of translation in the host organism, the intrinsic stability of the protein within the cell, etc., can affect the expression level, and can be manipulated using art-known methods. For example, transcriptional regulatory sequences, such as promoters, enhancers or other expression control elements, are known in the art (see, e.g., Goeddel, Gene Expression Technology: Methods in Enzymology 185, Academic Press (1990)). It will be appreciated by those skilled in the art that the design of the expression vector, including the selection of regulatory sequences may depend on such factors as the choice of the host cell to be transformed, the level of expression of protein desired, etc.

In certain embodiments, the expression level of the methylase (hence the methylation level of a DNA) is modulated by the strength of the promoter. Many promoter sequences suitable for bacterial hosts are known in the art, such as T3, T5, T7, Lac, lacZ, Trp, Gpt, lambda, PR, PL. The strengths of bacterial promoters have been reported. See e.g., Eeuschle et al., Promoters of *Escherichia coli*: a hierarchy of in vivo strength indicates alternate structures, The EMBO Journal, 5:2987-2994 (1986); Rhodius et al., Predicting strength and function for promoters of the *Escherichia coli*: alternative sigma factor, PNAS, 107: 2854-2859 (2010). Liang et al. (Activities of constitutive promoters in *Escherichia coli*., J Mol Biol. 1999 Sep. 10; 292(1):19-37) discloses seven constitutive promoters in *Escherichia coli*. The promoters include (i) the spc ribosomal protein operon promotor Pspc; (ii) the beta-lactamase gene promotor Pblaof plasmid pBR322; (iii) the PLpromoter of phage lambda; (iv) and (v) the replication control promoters PRNAI and PRNAII of plasmid pBR322; and (vi) and (vii) the P1 and P2 promoters of the rrnB ribosomal RNA operon. The strength of the promoters are also disclosed. All of these promoters are suitable for use for the subject technology.

Alternatively or in addition, the expression level of the methylase (hence the methylation level of a DNA) can modulated by the ribosome-binding site (RBS). Generally, the stronger the binding of the mRNA to the ribosomal RNA, the greater the efficiency of translational initiation. Activity of a RBS can be influenced by the length and nucleotide composition of the spacer separating the RBS and the initiator AUG. Bacterial mRNAs that do not have a close match to the consensus ribosome attachment sequence are not translated efficiently.

The expression of methylase in a microbial host described herein can be further improved by codon-optimization. For example, modifying a less-common codon with a more common codon may affect the half-life of the mRNA or alter its structure by introducing a secondary structure that interferes with translation of the message. All or a portion of a coding-region can be optimized. In some cases the desired modulation of expression is achieved by optimizing essentially the entire gene. In other cases, the desired modulation will be achieved by optimizing part of but not entire sequence of the gene.

The half-life of methylase may also be modulated, for example, by create a fusion protein in which the methylase is fused with a stable host protein.

C. Incorporating Methylase-Coding Sequence into Host Chromosome

Methods of incorporating the methylase-coding sequence (together with any regulatory sequences (such as transcriptional promoters and terminators, RBS, etc.) if desired) are known in the art. See, e.g., U.S. Pat. Nos. 5,695,976, 5,882,888. Generally, for integration, the exogenous DNA sequence should have some sequence homology for recombination between the exogenous DNA and the hose genome; the chromosome integration site should not be within an essential coding gene.

For example, a segment of DNA from the host chromosome can be cloned on a plasmid. The methylase-coding sequence (together with any regulatory sequences (such as transcriptional promoters and terminators, RBS, etc., if desired) can be inserted in the middle of this chromosome sequence. Homologous DNA pairing will then occur between plasmid-bourn host sequence and the host chromosome. A double cross over event will result in the integration of the methylase-coding sequence. In addition to sequences encoding the methylase and regulatory sequences, the plasmid may carry additional sequences, such as sequences that regulate replication of the vector in host cells (e. g., origins of replication) and selectable marker genes.

As described and exemplified herein, the inventors discovered that when the methylase gene sssI was introduced into an *E. coli* cell in the form of a plasmid, such that the plasmid was replicated in vivo, the methylase gene became toxic to the bacterial host. It is believed that when the plasmid was replicated in vivo, methylase was expressed at a dose that caused toxicity, killing the host cells before the plasmid could be integrated into the genome. Accordingly, the inventors replicated the plasmid in vitro, such that enough copies of sssI genes were directly introduced into the host cell without the need for in vivo replication. By this way, the sssI gene was integrated into the genome without the requirement of in vivo replication. Because of the low copy number of genome-integrated sssI gene (as compared to a copy number plasmid), the amount of methylase produced this way did not reach the toxic level.

Accordingly, some methods of the subject technology further include incorporating a gene toxic to an *Escherichia coli* (*E. coli*) bacteria controlled by a constitutive promoter, the method comprising (a) selecting a plasmid containing the gene toxic to *E. coli* and a selectable marker in the proper orientation; (b) amplifying the plasmid in vitro to produce a microgram quantity of the plasmid; (c) electroporating the plasmid into the *E. coli*; and (d) selecting the *E. coli* incorporating the gene toxic to the *E. coli*. Some methods provide that the amplifying is performed by a rolling circle amplification. Some methods provide that the gene toxic to *E. coli* comprises a methylase gene.

This method can be used to recombinantly express other genes that are toxic to the host. The toxicity of a recombinantly expressed protein can be influenced by, for example, the strength of the promoter, the copy number of the plasmid, the expression level of the protein, and the function of the protein, etc. Toxicity of a protein, and the threshold level of a toxic protein before it becomes detrimental to a host, can be assessed, for example, by determining the growth rate of the bacterial culture. As used herein, a gene is considered toxic or reaches a toxic level when the bacterial host, when expressing the gene beyond a threshold level, cannot divide or replicate to produce daughter cells. For example, a gene may be considered as a toxic gene if it cause the bacterial host to stop cell division when more than 1 copy, more than 2 copies, more than 3 copies, more than 4 copies, more than 5 copies, more than 10 copies, more than 15 copies, more than 20 copies, more than 30 copies, more than 40 copies, or more than 50 copies, of the gene are present in the bacterial host.

Site-specific integration is preferred over random integration, as the environment (sequence) of the integration site is known. The chromosome integration site disclosed in the Example is an "att" site. See, Haldimann et al., Conditional-Replication, Integration, Excision, and Retrieval Plasmid-Host Systems for Gene Structure-Function Studies of Bacteria, Journal of Bacteriology, vol 183, 6384-6393 (2001). The att site allows specific integration of the methylase coding sequence into the *E. coli* genome in single copies.

The plasmid may be transformed or transfected into a host cell by standard techniques, such as electroporation, calcium-phosphate precipitation, or DEAE-dextran transfection.

Bacterial strains described herein may be cultured in a suitable culture medium known in the art. Descriptions of culture media for various microorganisms can be found in the textbook "Manual of Methods for General Bacteriology" of the American Society for Bacteriology (Washington D.C., USA, 1981; the entirety of which is hereby incorporated herein by reference). These media which can be employed in accordance with the subject technology usually comprise one or more carbon sources, nitrogen sources, inorganic salts, vitamins and/or trace elements.

4. Use of Bacterial Strains

In another aspect, the bacterial strains described herein can be used to produce DNA with a desired methylation level. For example, a DNA molecule, such as a plasmid, produced by the bacterial strains described herein will have a methylation level that is closer to a mammalian DNA, thereby reducing the risk of triggering an immune response.

Some methods of the subject technology include preparing a modified plasmid for use as a DNA vaccine or a gene therapy agent comprising expressing a plasmid encoding a first gene in a bacterium having chromosomal DNA that comprises an engineered methylase gene controlled by a constitutive promoter stably incorporated into the chromosomal DNA. Some methods provide that the bacterium is *E. coli*.

In some embodiments, from about 10% to about 90% of the CpG dinucleotides of the DNA (such as a plasmid) produced by the bacterial strain described herein are methylated. For example, at least about 15%, at least about 20%, at least about 25%, at least about 30%, at least about 35%, at least about 40%, at least about 45%, at least about 50%, at least about 65%, at least about 70%, at least about 75%, at least about 80%, at least about 85%, at least about 90%, from about 10% to about 90%, from about 15% to about 80%, from about 15% to about 70%, from about 15% to about 60%, from about 15% to about 50%, from about 10% to about 50%, from about 15% to about 45%, from about 10% to about 45%, from about 15% to about 40%, from about 10% to about 40%, from about 15% to about 35%, from about 10% to about 35%, from about 15% to about 30%, from about 10% to about 30%, from about 15% to about 25%, from about 10% to about 25%, from about 25% to about 50%, from about 25% to about 45%, from about 25% to about 40%, from about 25% to about 35%, or from about 25% to about 30%, of the CpG dinucleotides of the DNA (such as a plasmid) produced by the bacterial strain described herein are methylated.

DNA molecules, such as plasmids, produced by the bacterial strains described herein can also be used for treating allergy, an autoimmune disease, or cancer. Some methods provide that the DNA molecule comprises a gene encoding at least one of an allergen, an autoantigen, a cancer antigen, a donor antigen, or a pro-apoptotic protein. Some methods provide that the DNA molecule comprises a polynucleotide sequence encoding an allergen or an antigenic fragment thereof, an autoantigen or an auto-antigenic fragment thereof, a cancer antigen or an antigenic fragment thereof, a donor antigen or an antigenic fragment thereof, or a pro-apoptotic protein or a functional fragment thereof. Any combinations of these proteins or fragments are also encompassed.

Autoantigens include any self antigens that the host or patient immune system recognizes and responds against as foreign including, e.g., self antigens associated with an autoimmune disorder. Some methods provide that the autoantigen is selected from the group consisting of carbonic anhydrase II, chromogranin, collagen, CYP2D6 (cytochrome P450, family 2, subfamily Device 400, polypeptide 6), glutamic acid decarboxylase, secreted glutamic acid decarboxylase 55, hCDR1, HSP60, IA2, IGRP, insulin, myelin basic protein, hNinein, Ro 60 kDa, SOX-10 (SRY-box containing gene 10), and ZnT8. An antigenic fragment (such as an epitope) of any one of these auto-antigens is also encompassed. Additional examples of autoantigens are listed below.

Some methods provide that the allergen is selected from the group consisting of peanut allergens Ara h 1, 2 and 3; pollen allergens Phl p 1, 2, 5a, 5b, 6, and Bet v 1; and cat allergen Fel d 1. Some methods provide that the donor antigens are a major or a minor histocompatibility complex molecule. An antigenic fragment of any one of these allergens is also encompassed.

| Autoimmune Disease | Self-Antigen | Number mRNA | Reference |
|---|---|---|---|
| Multiple Sclerosis | proteolipid protein PLP-1 | NM_000533 | J. Neurosci Res. 2001 Feb. 1; 63(3): 290-302 |
| | myelin basic protein | NM_002385 | J Neurosci Res. 2001 February 63(3): 290-302 |
| | Myelin associated oligodendrocytic basic protein | NM_006501 | J. Neurochem. 88 (5), 1211-1219 (2004); J. Biol. Chem. 269 (50), 31725-31730 (1994) |
| | Myelin-associated glycoprotein | NM_002361; NM_080600 | J. Neuropathol. Exp. Neurol. 62 (1), 25-33 (2003); J. Neurosci. Res. 24(2), 137-142 (1989) |
| | Alpha-B-crystallin | NM_001885 | J. Neurosci. Res. 75 (4), 516-523 (2004) |
| | Cyclic nucleotide phosphodiesterase | NM_033133 | |
| | myelin oligodendrocyte glycoprotein | NM_002433 | J. Neurosci Res. 2001 February 63(3): 290-302 |
| Type 1 Diabetes Mellitus | Pre-proinsulin/ pro-insulin/insulin | NM_000207 | Proc Natl Acad Sci USA 2003 Sep. 2; 100(18): 10376-81. Epub 2003 Aug. 18 |
| | glutamic acid decarboxylase 2 (65 kDa and 67 kDa forms) | NM_000818 | J Autoimmun. 2003 May; 203): 203-6 |
| | Tyrosine phosphatase IA2, IA-2β | NM_002846 | |
| | Carboxypeptidase H | | |
| | Heat shock proteins | | |
| | Glima 38 | | J. Clin. Invest. 1996 June; 15: 97(12): 2772-83 |
| | Islet cell antigen 69 kDA | | J. Biol. Chem; 2003 July; 11: 278(28): 26166-73 |
| | P52 | | J. Autoimmun. 1997 August; 1-(4): 387-94 |
| | Islet cell glucose transporter GLUT-2 | J03810 | |
| Guillian Barrre Syndrome | Peripheral myelin protein I (and others) | | |
| Myasthenia Gravis | cholinergic receptor α-chain | NM_005199 | Ann NY Acad Sci. 2003 September; 998: 284-307 |
| Autoimmune Thyroiditis | Thyoglobulin | NM_003235 | Int Rev Immunol. 2000; 19(6): 501-33 |
| | Thyroid peroxidase | AF439430 | |
| Rheumatoid Arthritis | Type I, II, III, IV, V, IX and XI collagens | NM_001844 | J Rheumatol. 2000 March; 27(3): 589-93 |
| | Immunoglobulin | | |
| | fibrin | | |
| | filaggrin | XM_048104 | |
| | GP-39 | XM_001276 | Genomics 43 (2), 221-225 (1997) |
| | hnRNPs | | |
| | matrix metalloproteinase MMP-1 | NM_002412 | J Rheumatol, 2003 June; 30(6): 1147-56 |

-continued

| Autoimmune Disease | Self-Antigen | Number mRNA | Reference |
|---|---|---|---|
| Autoimmune Uveitis | S-antigen Interphotoreceptor retinoid binding protein (IRBP) rhodopsin recoverin | M22453 | |
| Primary Biliary Cirrhosis | Pyruvte dehydrogenase complexes (2-oxoacid dehydrogenase) | | |
| Autoimmune hepatitis | Liver hepatocyte antigens Cytochrome p450 | | |
| Pemphigus vulgaris | Desmoglein-1, −3 (and others) | NM_001942 NM_001944 | |
| Autoimmune gastritis | H+/ K+ ATPASE Intrinsic factor | | Eksp Klin Gastroenterol. 2003; (3): 5-6, 116. |
| Pernicious Anemia | Intrinsic factor | | |
| Polymyositis | Histidyl tRNA synthetase, Other synthetases Other nuclear antigens | NM_002109 | |
| Grave's disease | Thyroid-stimulating hormone receptor | NM_000369 | |
| Psoriasis | | | |
| Vitiligo | Tyrosinase Tyrosinase-related protein-2 | NM_000372 NM_000550 | |
| Systemic Lupus Eryth. | Systemic nuclear antigens DNA histones ribonucleoproteins | | |
| Celiac disease | Transglutaminase | NM_198951 | J. Biol. Chem. 277 (37), 34109-34116 (2002) |

Some methods provide that the cancer antigen is selected from the group consisting of HER-2, gp100, melan A and PSA. Other cancer or tumor antigens include, e.g., (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Lewis x (associated with, e.g., breast and colorectal cancer) as well as various mucins; glycoproteins are coupled to a carrier protein (e.g., MUC-1 are coupled to KLH); (ii) lipopolypeptides (e.g., MUC-1 linked to a lipid moiety); (iii) polysaccharides (e.g., Globo H synthetic hexasaccharide), which are coupled to a carrier proteins (e.g., to KLH), (iv) gangliosides such as GM2, GM12, GD2, GD3 (associated with, e.g., brain, lung cancer, melanoma), which also are coupled to carrier proteins (e.g., KLH). An antigenic fragment of any one of these cancer antigens is also encompassed.

Some methods provide that the pro-apoptotic protein is selected from the group consisting of BAK, BAX, BIM, a modified caspase, Death Receptor 3 (DR3), Death Receptor 4 (DR4), Death Receptor 5 (DR5), a FAS receptor, a modified survivin protein, and a Tumor Necrosis Factor Receptor. A functional fragment of any one of these pro-apoptotic proteins is also encompassed.

Some methods described here provide ways for increasing the expression of regulatory T cells (Tregs) in a mammal comprising contacting the mammal with a modified plasmid generated in a bacterium having chromosomal DNA comprising an engineered methylase gene controlled by a constitutive promoter stably incorporated into the chromosomal DNA. Some methods provide that the bacterium is E. coli.

Some methods provide that the modified plasmid encodes an allergen, an autoantigen, a donor antigen, or a pro-apoptotic protein. Some methods provide that the DNA molecule comprises a polynucleotide sequence encoding an allergen or an antigenic fragment thereof, an autoantigen or an auto-antigenic fragment thereof, a cancer antigen or an antigenic fragment thereof, a donor antigen or an antigenic fragment thereof, or a pro-apoptotic protein or a functional fragment thereof. Any combinations of these proteins or fragments may also be used.

Some methods provide that the autoantigen is selected from the group consisting of carbonic anhydrase II, chromogranin, collagen, CYP2D6 (cytochrome P450, family 2, subfamily Device 400, polypeptide 6), glutamic acid decarboxylase, secreted glutamic acid decarboxylase 55, hCDR1, hNinein, HSP60, IA2, IGRP, insulin, myelin basic protein, Ro 60 kDa, SOX-10 (SRY-box containing gene 10), and ZnT8. Antigenic fragments of the foregoing autoantigens may also be used. Other autoantigens described herein may also be used. Some methods provide that the pro-apoptotic protein is selected from the group consisting of BAK, BAX, BIM, a modified caspase, Death Receptor 3 (DR3), Death Receptor 4 (DR4), Death Receptor 5 (DR5), a FAS receptor, modified surviving protein, and Tumor Necrosis Factor Receptor. A functional fragment of any one of these pro-apoptotic proteins may also be used.

For different purposes, the methylation level may need to be adjusted or optimized. For example, U.S. Pat. Pub. No. 2009/0191218 (Escher et al.) discloses the use of methylated plasmid for treating skin graft. In the skin graft model reported therein, about 50% of the CpG dinucleotides in the plasmid were methylated. The plasmid was effective in treating skin transplant rejection. In comparison, in Examples 2 and 6 described herein, a 4:2 (hypermethylated: hypomethylated) mixture of two plasmids, which results in about 40% to 45% of CpG methylation, achieved the best result in treating Type I diabetes. Therefore, while the methylation level may need to be adjusted or optimized or different types of treatment, the screening or assessing such level can be achieved using art known methods.

Similar rationales may be applied to the use of methylated DNA (e.g., plasmid) as described herein for gene therapy. For gene therapy, two considerations may be made with respect to optimal or desired methylation level. First is whether the foreign DNA would elicit immune response to host cell, as described above. Second is how the expression level of the foreign gene would be affected by methylation. Often, for gene therapy, the expression of the foreign gene is controlled by a tissue-specific promoter that is activated in specific tissues. Some tissue-specific promoters may be more sensitive to methylation regulation than others. Nagase et al., (Epigenetics: differential DNA methylation in mammalian somatic tissues, FEBS Journal 275 (2008) 1617-1623) discloses different levels of promoter methylation in different mammalian tissues. One may take into consideration differences in promoter methylation in different tissues when determining a desired methylation level for gene therapy. Reyes-Sandoval et al. (CpG Methylation of a Plasmid Vector Results in Extended Transgene Product Expression by Circumventing Induction of Immune Responses, Molecular Therapy Vol. 9, 246-261 (2004)) reports the use of a CpG-methylated plasmid expression vector expressing the highly immunogenic glycoprotein of rabies virus in order to achieve prolonged transgene product expression by circumventing immune recognition. Their data show that mice inoculated with a CpG-methylated plasmid expression vector show delayed clearance of transfected cells and fail to mount a strong immune response to the transgene product. Gene transfer with a CpG methylated plasmid resulted in a state of immunological low responsiveness to the transgene product, which may facilitate readministration of the transgene.

Accordingly, DNA molecules, such as plasmids, produced by the bacterial strains described herein can be used for gene therapy. The plasmids used in gene therapy may carry (i) an origin of replication, (ii) a marker gene such as a gene for resistance to an antibiotic (kanamycin, ampicillin, and the like) and (iii) one or more transgenes with sequences necessary for their expression (enhancer(s), promoter(s), polyadenylation sequences, and the like).

In another aspect, the subject technology provides a method of adjusting methylation level of a DNA plasmid for treating an autoimmune disease, wherein said DNA plasmid encodes an autoantigen or an antigenic fragment thereof, and is produced by a bacterium described herein, comprising: (i) administering said DNA plasmid to a subject in need thereof; (ii) determining a therapeutic effect of said DNA plasmid; and (iii) adjusting a methylation level of said DNA based on the therapeutic effect.

In another aspect, the subject technology provides a method of adjusting methylation level of a DNA plasmid for treating a transplant recipient, wherein said DNA plasmid encodes a donor antigen or an antigenic fragment thereof, and is produced by a bacterium described herein, comprising: (i) administering said DNA plasmid to a subject in need thereof; (ii) determining a therapeutic effect of said DNA plasmid; and (iii) adjusting a methylation level of said DNA based on the therapeutic effect.

In another aspect, the subject technology provides a method of adjusting methylation level of a DNA plasmid for gene therapy, wherein said DNA plasmid encodes a therapeutic protein and is operably linked to a promoter, and is produced by a bacterium described herein, comprising: (i) administering said DNA plasmid to a subject in need thereof; (ii) determining a therapeutic effect of said DNA plasmid; and (iii) adjusting a methylation level of said DNA based on the therapeutic effect.

In another aspect, the subject technology provides a method of expressing a protein of interest in a target cell or target tissue of a subject, comprising: administering a plasmid DNA to a subject in need thereof, wherein said plasmid DNA comprises a polynucleotide that encodes a therapeutic protein, and is operably linked to a promoter, wherein said promoter can be activated in the target cell or target tissue, and wherein said DNA plasmid is produced by the bacterium described herein.

In another aspect, the subject technology provides a method of providing a DNA plasmid for expressing a protein of interest in a target cell or target tissue of a subject, comprising: (i) selecting a promoter that can be activated in the target cell or target tissue; (ii) determining a methylation level for said promoter, such that a transcriptional repression of the promoter by methylation is no more than 70% (preferably, no more than 60%, no more than 50% no more than 40% no more than 30% no more than 20%, or no more than 10%); (iii) operably linking said promoter to a polynucleotide sequence encoding said protein of interest to create a DNA plasmid; (iv) producing said DNA plasmid using a bacterium described herein, according to the methylation level determined in step (ii).

Generally, methylation of a promoter represses the activity or strength of the promoter. Preferably, methylation level of the promoter is determined such that methylation represses the activity or strength of the promoter by no more than 50%, as compared to the activity or strength of the promoter prior to methylation (that is, when the methylation level of the promoter is about 15% or less, preferably 10% or less). Alternatively or in addition, the methylation level of a promoter sequence is about 60% or less, about 55% or less, about 50% or less, about 45% or less, about 40% or less, about 35% or less, about 30% or less, about 25% or less, or about 20% or less, such that the activity or strength of the promoter is not significantly repressed, and the protein of interest is expressed at a sufficient level. The activity or strength of a methylated promoter vs. a corresponding unmethylated (hypomethylated) promoter can be compared, for example, by comparing the quantities of mRNAs transcribed from an operably linked coding sequence.

In one embodiment, the subject technology includes a kit for preparing a plasmid for use as a DNA vaccine or a recombinant gene therapy agent comprising: (a) a bacterium having chromosomal DNA comprising an engineered methylase gene controlled by a constitutive promoter stably incorporated into the chromosomal DNA; and (b) instructions for use in expressing a plasmid encoding a gene of interest. In various embodiments, the bacterium comprises E. coli.

Being a negatively charged, high molecular weight molecule, DNA has difficulties in passing spontaneously through the phospholipid cell membranes. Various vectors are hence used in order to permit gene transfer: viral vectors on the one hand, natural or synthetic chemical and/or biochemical vectors on the other hand. Viral vectors (retroviruses, adenoviruses, adeno-associated viruses, etc.) are very effective, in particular for passing through the membranes, but present a number of risks, such as pathogenicity, recombination, replication, immunogenicity, and the like. Chemical and/or biochemical vectors enable these risks to be avoided. They are, for example, cations (calcium phosphate, DEAE-dextran, and the like) which act by forming precipitates with DNA, which precipitates can then be "phagocytosed" by the cells. They can also be liposomes in which the DNA is incorporated and which fuse with the plasma membrane. Synthetic gene transfer vectors are generally cationic lipids or polymers which complex DNA can form therewith a particle carrying positive surface charges. These particles are capable of interacting with the negative charges of the cell membrane and then of crossing the latter. Examples of such vectors can include dioctadecylamido-glycylspermine (DOGS, Transfectam™) or N-[1-(2,3-diol-eyloxy)propyl]-N,N,N-trimethylammonium chloride (DOTMA, Lipofectin™). Chimeric proteins have also been developed: they consist of a polycationic portion which condenses the DNA, linked to a ligand which binds to a membrane receptor and gives rise to the complex in the cells by endocytosis. It is thus theoretically possible to "target" a tissue or certain cell populations in order to improve the in vivo bioavailability of the transferred gene.

5. Methods of Treatment

One aspect of the subject technology describes methods to enhance the potency of DNA vaccines for the treatment of various immune-mediated inflammatory disorders, including rejection of solid organ transplants, graft versus host disease, host versus graft disease, autoimmune hepatitis, vitiligo, diabetes mellitus type 1, Addison's Disease, Graves' disease, Hashimoto's thyroiditis, multiple sclerosis, polymyalgia rheumatica, Reiter's syndrome, Crohn's disease, Goodpasture's syndrome, Gullain-Barre syndrome, lupus nephritis, rheumatoid arthritis, systemic lupus erythematosus, Wegener's granulomatosis, celiac disease, dermatomyositis, eosinophilic fasciitis, idiopathic thrombocytopenic purpura, Miller-Fisher syndrome, myasthenia gravis, pemphigus vulgaris, pernicious anaemia, polymyositis, primary biliary cirrhosis, psoriasis, psoriatic arthritis, rheumatoid arthritis, Sjögren's syndrome, and the like.

As described herein, different levels of DNA methylation may be desired for different applications. Levels of methylation can be modulated at least by two ways. First, it can be achieved by modulating the expression level of methylase (e.g., by using promoters of different strength). Second, it may be achieved by mixing hypermethylated DNA (e.g., DNA in which about 50% of the CpG dinucleotides are methylated) with hypomethylated DNA (e.g., DNA in which about 10% to about 15% of the CpG dinucleotides are methylated), and adjusting ratios of the hypermethylated DNA to hypomethylated DNA.

In one aspect, the subject technology provides a method for treating an autoimmune disease, comprising administering to a subject in need thereof a therapeutically effective amount of: (a) a first polynucleotide comprising a sequence that encodes an autoantigen, or an antigenic fragment thereof, wherein at least about 70%, at least about 65%, at least about 60%, at least about 55%, at least about 50%, at least about 45%, at least about 40%, at least about 35%, at least about 30%, or at least about 25% of the CpG dinucleotides of said first polynucleotide are methylated; and (b) a second polynucleotide comprising a sequence that encodes a pro-apoptotic protein, or a functional fragment thereof; wherein about 10% or less, about 5% or less, about 3% or less, or about 1% or less, of the CpG dinucleotides of said second polynucleotide are methylated.

In various embodiments, said first polynucleotide and second polynucleotide are administered at a ratio of from about 10:1 to about 1:10 (μg:μg). In exemplary embodiments, the ratios are from about 4:1 to about 4:2 (μg:μg). Other suitable ratios include, e.g., about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, from about 5:1 to about 1:5, from about 5:1 to about 1:3, from about 5:1 to about 1:1, from about 5:1 to about 2:1, or from about 4:1 to about 1:1, etc.

Optimal or preferred range of ratios of the two DNAs may be determined by a skilled person using known screening methods. For example, as exemplified herein, different ratios of hypermethylated sGAD-coding sequence (msGAD) to hypomethylated BAX-coding sequences (BAX) were screened using NOD mice. It was discovered, based on percentage of diabetic incidence, that a mixture at 4:2 ratio provides superior results as compared to 4:1 ratio. Similar screening assays can be applied to assess and optimize the ratios of hypermethylated DNA and hypomethylated DNA.

In another aspect, the subject technology provides a method for treating an autoimmune disease, comprising administering to a subject in need thereof a therapeutically effective amount of: (a) a first polynucleotide comprising a sequence that encodes an autoantigen, or an antigenic fragment thereof; and (b) a second polynucleotide comprising a sequence that encodes a pro-apoptotic protein, or a functional fragment thereof; wherein from about 10% to about 50% of the CpG dinucleotides of said first and second polynucleotide are methylated. Preferably, from about 25% to about 45%, from about 30% to about 45%, from about 35% to about 45%, or from about 40% to about 45% of the CpG dinucleotides of said first and second polynucleotide are methylated.

The first polynucleotide and the second polynucleotide may be the same polynucleotide (i.e., a polynucleotide encoding both proteins), or may be different (i.e., two polynucleotides, one encoding the autoantigen, and the other encoding the pro-apoptotic protein). If the two proteins are encoded by two different polypeptides, the methylation levels of the two polynucleotide can be different, as long as the combined CpG methylation level is within a desired range. For example, if about 42% of CpG methylation is desired, one can mix the first polynucleotide (at about 50% CpG methylation level) with the second polynucleotide (at about 10% CpG methylation level), at about 4:1 ratio, to achieve a final CpG methylation level at about 42%.

Suitable autoantigens for certain autoimmune diseases are described in the Table above. Suitable pro-apoptotic proteins are also described above.

In certain embodiments, the autoimmune disease is Type I diabetes. In certain embodiments, the autoantigens is said autoantigen is glutamic acid decarboxylase (GAD), a secreted form of GAD (sGAD), or an auto-antigenic fragment thereof. Nucleic acid sequences encoding human GAD, and a secreted form of human GAD, are provided herein as SEQ ID NO:1 and NO:2, respectively. In certain embodiments, the pro-apoptotic protein is BAX, or a functional fragment thereof.

In various embodiments, when the method comprises administering one or more than one immunosuppressant agent(s), the one or more than one immunosuppressant agent(s) can be administered simultaneously, separately or sequentially.

In various embodiments, the one or more than one immunosuppressant agent(s) may be selected from the group consisting of corticosteroids, glucocorticoids. cyclophosphamide, 6-mercaptopurine (6-MP), azathioprine (AZA), methotrexate cyclosporine, mycophenolate mofetil (MMF), mycophenolic acid (MPA), tacrolimus (FK506), sirolimus ([SRL] rapamycin), everolimus (Certican), mizoribine, leflunomide, deoxyspergualin, brequinar, azodicarbonamide, vitamin D analogs, such as MC1288 and bisindolyl-maleimide VIII, antilymphocyte globulin, antithymocyte globulin (ATG), anti-CD3 monoclonal antibodies, (Muromonab-CD3, Orthoclone OKT3), anti-interleukin (IL)-2 receptor (anti-CD25) antibodies, (Daclizumab, Zenapax, basiliximab, Simulect), anti-CD52 antibodies, (Alemtuzumab, Campath-1H), anti-CD20 antibodies (Rituximab, Rituxan), anti-tumor necrosis factor (TNF) reagents (Infliximab, Remicade, Adalimumab, Humira), LFA-1 inhibitors (Efalizumab, Raptiva), and the like.

In one embodiment, the method further comprises, after administering the DNA vaccine, monitoring the recipient for rejection of the allograft of transplant. In a preferred embodiment, the recipient is monitored for rejection of the allograft or transplant after tapering off or discontinuing the administration of immunosuppressant agent(s).

For administration to a subject, polynucleotides disclosed herein are generally formulated in a composition suitable for in vivo administration. Such compositions generally include a carrier that can is acceptable for formulating and administering the agent to a subject. Such acceptable carriers are well known in the art and include, for example, aqueous solutions such as water or physiologically buffered saline or other solvents or vehicles such as glycols, glycerol, oils such as olive oil or injectable organic esters. An acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of an acceptable carrier, including a physiologically acceptable compound, depends, for example, on the physico-chemical characteristics of the therapeutic agent and on the route of administration of the composition, which can be, for example, orally or parenterally such as intravenously, and by injection, intubation, or other such method known in the art. The pharmaceutical composition also can contain a second reagent such as a diagnostic reagent, nutritional substance, toxin, or therapeutic agent, for example, a cancer chemotherapeutic agent.

Polynucleotides described herein can be incorporated within an encapsulating material such as into an oil-in-water emulsion, a microemulsion, micelle, mixed micelle, liposome, microsphere or other polymer matrix (see, for example, Gregoriadis, Liposome Technology, Vol. 1 (CRC Press, Boca Raton, Fla. 1984); Fraley, et al., Trends Biochem. Sci., 6:77 (1981)). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212) are an example of such encapsulating materials particularly useful for preparing a composition useful in a method of the invention, and other "masked" liposomes similarly can be used, such liposomes extending the time that the therapeutic agent remain in the circulation. Cationic liposomes, for example, also can be modified with specific receptors or ligands (Morishita et al., J. Clin. Invest., 91:2580-2585 (1993), which is incorporated herein by reference). In addition, a polynucleotide can be introduced into a cell using, for example, adenovirus-polylysine DNA complexes (see, for example, Michael et al., J. Biol. Chem. 268:6866-6869 (1993)).

The route of administration of the composition containing polynucleotides described herein will depend, in part, on the chemical structure of the molecule. Polypeptides and polynucleotides, for example, are not particularly useful when administered orally because they can be degraded in the digestive tract. However, methods for chemically modifying polypeptides, for example, to render them less susceptible to degradation by endogenous proteases or more absorbable through the alimentary tract are disclosed herein or otherwise known in the art (see, for example, Blondelle et al., supra, 1995; Ecker and Crook, supra, 1995). In addition, a polypeptide can be prepared using D-amino acids, or can contain one or more domains based on peptidomimetics, which are organic molecules that mimic the structure of a domain; or based on a peptoid such as a vinylogous peptoid.

A composition as disclosed herein can be administered to an individual by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the composition can be administered by injection, intubation, orally or topically, the latter of which can be passive, for example, by direct application of an ointment, or active, for example, using a nasal spray or inhalant, in which case one component of the composition is an appropriate propellant. A pharmaceutical composition also can be administered to the site of a pathologic condition, for example, intravenously or intra-arterially into a blood vessel supplying a tumor.

The total amount of the polynucleotide to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the composition to treat a pathologic condition in a subject depends on many factors including the age and general health of the subject as well as the route of administration and the number of treatments to be administered. In view of these factors, the skilled artisan would adjust the particular dose as necessary. In general, the formulation of the composition and the routes and frequency of administration are determined, initially, using Phase I and Phase II clinical trials.

The composition can be formulated for oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

In one embodiment, the method further comprises administering a dose of one or more than one immunosuppressant agent before, on the day of, and/or after engraftment or transplantation.

The dosages of the immunosuppressant agents will vary depending on the individual to be treated, the route of administration, and the nature and severity of the condition to be treated. For example, according to a particular embodiment, an initial dose of about 2 to 3 times the maintenance dose may suitably be administered about 4 to 12 hours before transplantation, followed by a daily dosage of 2 to 3 times the maintenance dose for one to two weeks, before gradually tapering down at a rate of about 5% a week to reach the maintenance dose.

The skilled person may determine those dosages that provide a therapeutic amount of an immunosuppressant agent at a level that is tolerated. In a preferred embodiment, the method further comprises administering a single dose of antilymphocyte globulin, of about 1.6 mg/20 g of body weight on the day of engraftment or transplantation. In another preferred embodiment, rapamycin may be applied at a dosage range of from about 0.05 to about 15 mg/kg/day, more preferably from about 0.25 to about 5 mg/kg/day, and most preferably from about 0.5 to about 1.5 mg/kg/day. Ideally, the administration of doses of one or more than one immunosuppressant agent(s) can be curtailed after effective treatment with the DNA vaccine. Kits with same or different dosage forms may be provided.

The following Examples provide further illustrations of the subject technology and are not intended to limit the scope of the subject technology.

Examplification

Example 1

Preparation of E. Coli with a Constitutive Methylase Gene

Two different strains of the bacterium *Escherichia coli*, DH5-alpha and GM2929, were engineered to carry the sssI gene encoding the CpG DNA methylase from Spiroplasma sp. strain MQ1 (M. SssI) (Renbaum et al., 1990 Nucleic Acids Res 18: 1145-1152) under the transcriptional control of a constitutive promoter. For this purpose, two plasmid DNA constructs part of the CRIM vector system previously described by Haldimann and Wanner were selected as molecular tools for chromosomal integration of the sssI gene (Haldimann and Wanner 2001 *J. Bacteriology* 183: 6384-6393).

The two components of the CRIM system that were selected are the pAH162 CRIM plasmid and the pAH123 CRIM helper plasmid. Plasmid pAH162 carries a tetracycline resistance gene, a multiple cloning site, a strain-restricted origin of replication, and the DNA attachment site from phage Φ80 (attPΦ80) which permits integration of the plasmid DNA into the single attPΦ80 site found in an *E. coli* chromosome. Plasmid pAH123 is a helper plasmid DNA construct carrying an ampicillin resistance gene and the $int_{\Phi 80}$ gene, which encodes the phage Φ80 integrase that catalyzes recombination between attPΦ80 sites. In addition, expression of $int_{\Phi 20}$ is induced after incubation of *E. coli* cells at 37° C. which is a non-permissive temperature for plasmid pAH123, i.e., the plasmid DNA is lost. In contrast, growth at 30° C. is permissive for the plasmid.

The initial plan for constructing the desired *E. coli* strains was to follow the general protocol described by Haldimann and Wanner. Specifically, the strategy was to clone the sssI gene into plasmid pAH162 and then use the construct to transform *E. coli* DH5-alpha and GM2929 cells previously transformed with helper plasmid pAH123. Cells would then be grown at 37° C. on medium containing the tetracycline antibiotic. Growth at that temperature would result in the synthesis of the Φ80 integrase encoded by the helper plasmid, which would in turn cause recombination between the pAH162-sssI plasmid and the *E. coli* chromosome at the attPΦ80 site and chromosomal integration of the plasmid DNA. Because plasmid pAH162 carries tetracycline resistance and cannot replicate in strains DH5-alpha and GM2929, presence of tetracycline-resistant colonies would indicate chromosomal integration of the plasmid DNA. In addition, helper plasmid pAH123 would be cured from the strains since it does not replicate at 37° C.

In order to clone the sssI gene into plasmid pAH162, a 280 bp BamHI-XbaI containing an undefined promoter sequence together the 5' end of the open-reading frame (ORF) coding for the SssI methylase was excised from plasmid pAIT2 (New England Biolabs, Ipswich, MA) and cloned into the BamHI-XbaI restriction sites of plasmid pAH162, generating plasmid pAH162-1. Then, a 980 bp Xba-I-XbaI DNA fragment containing the remaining ORF for SssI was excised from pAIT2 and cloned into the XbaI site of pAH162-1 in an effort to reconstitute the complete ORF coding for SssI. However, no *E. coli* clones containing the reconstituted ORF were obtained in spite of multiple attempts.

Because pAH162 and pAIT2 are high and low copy number plasmid DNA, respectively, it was hypothesized that the high copy number of the sssI gene carried by pAH162 was toxic to *E. coli* cells. Accordingly, a 1.3 kb PCR product containing the sssI gene and its undefined promoter sequence was amplified from plasmid pAIT2 and cloned into the ScaI site of the low copy number plasmid pACYC184. An *E. coli* clone containing pACYC184 carrying a 1.3 kb insert was obtained and restriction analysis indicated that the insert had the structural identity of the sss gene. Moreover, restriction analysis also confirmed that the plasmid DNA construct had increased levels of methylated CpG dinucleotides. Specifically, pACYC184 carrying the sssI gene (pACYC184-sssI) was isolated, digested with the restriction endonucleases HpaII and MspI, and analyzed using agarose gel electrophoresis. The HpaII and MspI endonucleases do not and do, respectively, digest DNA when their respective target sequence is CpG-methylated. Results indicated that the HpaII enzyme did not digest pACYC184 when it carried the 1.3 kb insert, but that the MspI enzyme digested pACYC184 whether or not the plasmid DNA carried the 1.3 kb insert. Therefore, results indicated that the 1.3 kb insert encoded a functional SssI methylase and that the high number of pAH162 prevented cloning of the sssI gene in that plasmid. Together, these results indicated that plasmid pAH162-sssI could not be amplified in *E. coli*, thereby limiting its use for integration of the sssI gene into the *E. coli* chromosome. Accordingly, means of constructing and producing pAH162-sssI plasmid DNA without amplification in *E. coli* were developed.

The first strategy consisted of excising a 1.7 kb BamHI-BsaBI DNA fragment containing the sssI gene+promoter sequence from pACYC184-sssI, to isolate and ligate in vitro the DNA fragment into plasmid pAH162 digested with BamI-SmaI, and to use the ligation mixture to transform directly *E. coli* DH5-alpha cells already carrying the pAH123 helper plasmid for selection at 37° C. on tetracycline-containing agar plates. However, no colonies were obtained using this approach. Control experiments revealed that only one tetracycline-resistant colony could be obtained after electroporation of 250 nanograms of undigested vector pAH162 alone, which indicated that an unrealistically large amount of ligation mixture would have to be used to obtain chromosomal integration. Accordingly, a second strategy was taken with the goal of obtaining large amounts of pAH162-sssI in vitro.

The second strategy consisted of cloning the 1.7 kb PCR fragment containing the sssI gene+promoter DNA sequence into pAH162, to obtain large amounts of the desired circular plasmid pAH162-sssI plasmid DNA construct alone from the ligation mixture in order to transform DH5-alpha and select for chromosomal integration. It was important to use only the circular form of pAH162-sssI because linear DNA could not be used for integration. Furthermore, it was also important to minimize contamination from other plasmid DNA forms because of the inherent low efficiency of chromosomal integration.

Accordingly, the following steps were devised and taken: The 1.7 kb PCR product containing the sssI gene+promoter DNA sequence was cloned into the SmaI site of plasmid pAH162. As a result, two different orientations of the 1.7 kb PCR insert were obtained. However, only one orientation could be used to proceed with amplification because subsequent manipulation of the amplified plasmid DNA would require digestion of the product with BamHI to obtain the linearized form of pAH162-sssI . Only one orientation of the PCR product could generate the linearized form of pAH162-sssI. The other orientation would have generated a DNA fragment corresponding to the sssI gene together with a separate DNA fragment corresponding to plasmid pAH162.

To ensure that the desired orientation alone would serve as a substrate for amplification, the ligation mixture containing originally the 1.7 kb PCR product and SmaI-treated pAH162 was digested with BamHI. Two oligonucleotides were then used to amplify selectively the linearized form of pAH162-sssI carrying the PCR insert in the desired orientation. The oligonucleotides hybridize to DNA sequences flanking one of the two BamHI sites that are found in close proximity to each other in the ligation product carrying the desired orientation of the PCR product insert. Therefore, synthesis of the ligation product with desired orientation is favored after PCR amplification. Following amplification with PCR, the 4.3 kb desired pAH162-sssI DNA product was digested with BamHI, fractionated using agarose gel electrophoresis, and directly isolated from the gel. See the schematic diagram in FIG. 1.

The isolated product was then used for its amplification in vitro in large amounts. Fifty nanograms of the isolated, BamHI-digested pAH162-sssI DNA was re-ligated for the purpose of multi-primed rolling circle amplification using the DNA polymerase from phage (29 according to a protocol derived from that described by Dean and co-workers (Dean et al., 2001 Genome Res 11: 1095). Specifically, 10 microliters of double-distilled water containing 50 nanograms of religated pAH162-sssI plasmid DNA were mixed with 4.4 microliters of 10× Φ29 DNA polymerase buffer (New England Biolabs), 0.5 microliters of 10× bovine serum albumin (0.1 milligram/milliliter final concentration), 4.4 microliters of random hexamer oligonucleotides (New England Biolabs, 50 micromolar final concentration), 22 microliters of 2 millimolar of each of the 4 dNTPs necessary for DNA synthesis, and double-distilled water for a total volume of 42.9 microliters. The mixture was kept at 70° C. for 5 minutes and then at 30° C. for 30 minutes to permit annealing of the hexamers to plasmid DNA strands. Following this incubation period, 1.1 microliter of Φ29 DNA polymerase (New England Biolabs, 10,000 units/milliliter) was added. The 44 microliters of prepared solution was gently mixed and incubated for 3 hours at 30° C. The reaction volume was then doubled every 3 hours using a solution consisting of the same original components but without plasmid DNA template. After 12 hours of incubation at 30° C., the reaction (352 microliters total volume) was stopped after incubation at 70° C. for 10 minutes. DNA was precipitated and total yield was estimated to be 140 micrograms using ultraviolet spectrophotometry. Presence of the 1.7 kb DNA fragment containing the sssI gene was then confirmed using PCR analysis.

Nine micrograms of the amplification product was then digested with BamHI and religated. Agarose gel electrophoresis confirmed that the correct size of pAH162-sssI plasmid DNA product had been obtained after amplification. Aliquots of one microgram of the re-ligated product were then used for electroporation of *E. coli* DH5-alpha carrying the pAH123 helper plasmid. Each microgram of the product yielded 2-4 tetracycline-resistant colonies growing at 37° C., which was consistent with our previous observation that 250 nanograms of vector pAH162 yielded 1 tetracycline-resistant colony. In contrast, electroporation of *E. coli* GM2929 cells with the same DNA product yielded 100 fold more colonies. FIG. 1 shows the scheme used to successfully incorporate the methylase gene into *E. coli* under the control of a constitutive promoter.

PCR analysis performed directly from bacterial cells confirmed the presence of the 1.7 kb DNA fragment carrying the sssI gene in the obtained colonies. Furthermore, PCR analysis was also performed to confirm integration and copy number of the 1.7 kb DNA fragment carrying the sssI gene following a procedure described previously by Haldimann and Wanner (Haldimann and Wanner, 2001 *J. Bacteriology* 183: 6384). Specifically, four oligonucleotides (P1, P2, P3, and P4, with P1 and P4 specific for the attPΦ80 integration site) were used together as primers in the PCR reaction. With these primers, a single DNA product indicates no integration, two DNA products indicate single-copy integration, and three DNA products indicate multiple integrations. Agarose gel electrophoresis of the PCR reactions performed with 16 DH5-alpha clones indicated that 14 clones contained a single integrated copy, one clone contained multiple copies, and one clone contained no integrated copy of the desired insert. A similar analysis of nine GM2929 clones indicated that all clones contained a single integrated copy.

Levels of CpG-methylation of plasmid DNA isolated from *E. coli* clones carrying a chromosomal copy of the sssI gene were then determined. Two DH-5a and two GM2929 clones carrying a single sssI gene insert were selected and transformed with a plasmid DNA construct. In addition, the same plasmid DNA construct was used to transform DH-5a and GM2929 cells that did not contain the sssI gene as control. Plasmid DNA was isolated and sent to EpigenDX (Worcester, MA) for pyrosequencing and determination of levels of CpG methylation of 11 CpG dinucleotide positions within the plasmid DNA. Results indicated mean CpG-methylation levels of control plasmid DNA from DH5-alpha cells not expressing the sssI gene were ~14-18% and that CpG-methylation levels from GM2929 cells not expressing the sssI gene were undetectable (See Table 1 below). In contrast, mean CpG-methylation levels from DH5-alpha and GM2929 cells carrying a single copy of the sssI gene were ~ 47-51% and ~ 49%, respectively. Together, these data show that *E. coli* strains carrying a chromosomal copy of the sssI gene synthesize plasmid DNA with increased levels of methylated CpG dinucleotides.

TABLE 1

| Well | Sample ID | Pos #1 | Pos #2 | Pos #3 | Pos #4 | Pos #5 | Pos #6 | Pos #7 | Pos #8 | Pos #9 | Pos #10 | Pos #11 | Mean | Stdev | Min | Max | Note |
|---|---|---|---|---|---|---|---|---|---|---|---|---|---|---|---|---|---|
| A1 | DH | 0.0 | 0.0 | 33.5 | 35.6 | 31.2 | 27.3 | 13.0 | 0.0 | 0.0 | 38.0 | 14.9 | 17.6 | 15.9 | 0.0 | 38.0 | Low signal |
| B1 | DH | 9.2 | 16.8 | 16.7 | 23.0 | 17.9 | 18.6 | 8.0 | 9.0 | 11.4 | 11.0 | 10.9 | 13.9 | 4.9 | 8.0 | 23.0 | |
| C1 | GM | — | — | — | — | — | — | — | — | — | — | — | | | | | (—)No signal |
| D1 | 3D | 50.8 | 54.3 | 62.8 | 69.3 | 53.6 | 47.2 | 24.6 | 46.7 | 59.0 | 47.9 | 46.9 | 51.2 | 11.5 | 24.6 | 69.3 | |
| E1 | 16D | 46.6 | 46.7 | 55.3 | 66.9 | 54.2 | 40.4 | 25.0 | 30.3 | 55.5 | 54.1 | 32.0 | 47.0 | 13.9 | 25.0 | 65.9 | Low signal |
| F1 | 16G | 48.2 | 50.1 | 61.4 | 66.2 | 50.0 | 44.1 | 22.1 | 44.7 | 60.0 | 45.4 | 45.6 | 48.9 | 11.7 | 22.1 | 65.2 | |
| G1 | 17G | 50.0 | 52.3 | 62.4 | 65.2 | 51.6 | 45.2 | 24.1 | 46.4 | 57.1 | 45.5 | 45.5 | 49.6 | 10.9 | 24.1 | 65.2 | |

Table 1 shows the percentage of methylated CpG dinucleotides at 11 positions and overall within a selected sequence of a plasmid DNA that was used to transform E. coli strains DH5-alpha (A1 and B1) and GM2929 (C1) as controls, and DH5-alpha and GM2929 derivative strains carrying a single chromosomal copy of the sssI gene, i.e., D1, E1 and F1, G1, respectively.

Example 2

Demonstration of Efficacy for Diabetes In Vivo

This Example and Example 6 show that partial hypermethylation of CpG dinucleotides carried by a plasmid DNA candidate product for therapy of T1D is unexpectedly superior to full hypermethylation of the same product for treatment of diabetes.

The DNA vaccines used in this Example and Example 6 composed of 2 plasmid DNA constructs. One construct encodes the pro-apoptotic protein BAX. The other construct encodes a secreted form of the pancreatic glutamic acid decarboxylase (sGAD), which is a T1D target autoantigen in both NOD mice and humans. The cDNAs coding for sGAD and BAX are both under transcriptional control of the SV40 promoter, which is still functional after CpG hypermethylation. Together, the 2 plasmid DNA constructs constitute a single product candidate for treatment of T1D.

The product candidate encodes 3 immune components that modulate pathways normally involved in maintaining immune tolerance and homeostasis in both mice and humans. The first encoded component is the BAX protein which induces formation of apoptotic cells in situ and which is named ADI for Apoptotic DNA Immunotherapy. ADI for induction of immune tolerance initiates the tolerogenic signal normally provided by the constant flux of apoptotic cells processed daily by dendritic cells (DCs) which maintain immune tolerance to peripheral tissues in mammals.

The second encoded component is hypermethylation of CpG dinucleotides in plasmid DNA which modulates the innate immune response and results in increased recruitment of plasmacytoid DCs (see below). Plasmid DNA hypermethylation is achieved using a proprietary strain of Escherichia coli DH5-alpha that carries the SssI methylase gene in its chromosome.

The third encoded component is sGAD autoantigen which modulates the adaptive immune response through induction of Tregs when combined with ADI. Both DCs and Tregs are essential leukocyte populations that control inflammation and establish as well as maintain immune tolerance to self antigens.

We previously showed that the 3 components are required in a synergistic manner to treat spontaneously hyperglycemic NOD mice successfully. Newly hyperglycemic mice, i.e., with different ages, received a weekly intradermal (i.d.) injections of 40 micrograms hypermethylated plasmid DNA coding for sGAD (msGAD) with 10 micrograms hypomethylated plasmid DNA coding for BAX (BAX) over 8 weeks. Results indicated that 80% of mice were diabetes-free at 40 weeks of age. Because of the beneficial effect of hypermethylation of the plasmid DNA construct coding for sGAD on treatment, we reasoned that hypermethylation of both plasmid DNA constructs would lead to improved therapeutic efficacy. The hypothesis was tested using treatment of 16-week-old NOD mice. Treating mice at this age is stringent because DNA is delivered in animals with different levels of disease and beta-cell mass.

For 8 weeks, 16-week-old female NOD mice received a weekly intradermal (i.d.) injection of: 50 micrograms of DNA vaccines consisting of 40 micrograms methylated plasmid DNA coding for secreted glutamic acid decarboxylase (mSGAD) and 10 micrograms plasmid DNA coding for the pro-apoptotic protein BAX, where the DNA was either unmethylated/hypomethylated (BAX) or methylated/hypermethylated (mBAX). See Li et al. 2006 Vaccine 24: 5036-5046 and U.S. Pat. Pub. No. 2008/0194510 (Escher et al.) for additional experimental details. It is expected that about 10%-15% of CpG dinucleotides were methylated for the "BAX" group, and about 50% of CpG dinucleotides were methylated for the "mBAX" group. For convenience, the "msGAD+mBAX" group are sometimes referred to as "fully" hypermethylated; and the "msGAD+BAX" group are sometimes referred to as "partially" hypermethylated.

Figure 2:
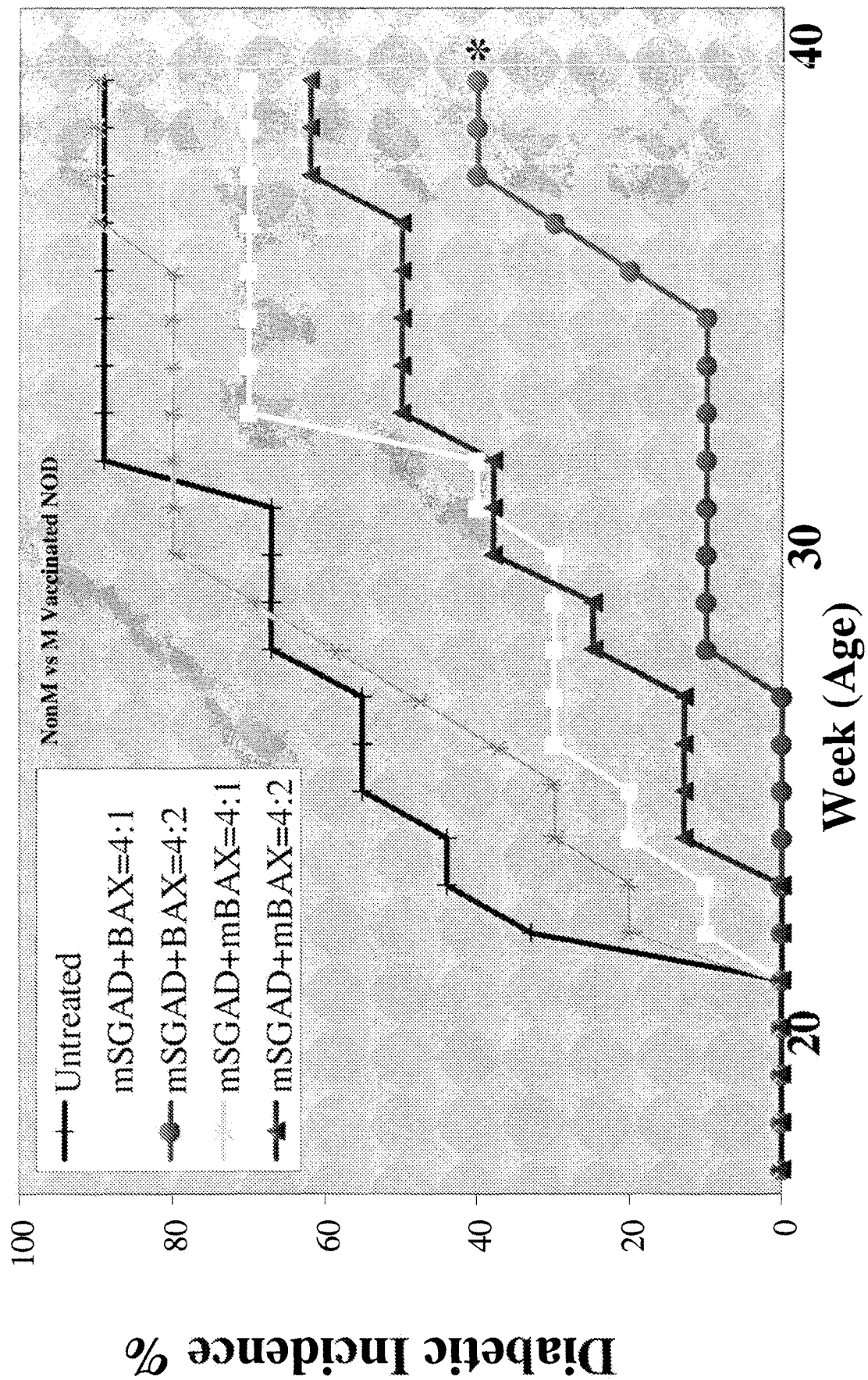
FIG. 2 shows the treatment efficacy of type 1 diabetes using plasmid DNA methylated with a DH5-alpha E. coli strain carrying a single copy of the sssI gene in its chromosome and the effect of methylation levels of the plasmid DNA vaccine on treatment efficacy. The graph illustrates the onset of diabetes in 16-week-old NOD mice receiving two different ratios of hypo- or hyper-methylated, bivalent pro-apoptotic DNA vaccines. Mice (N=10/group) received a single weekly i.d. injection of the indicated DNA at 16 weeks of age for 8 weeks and were monitored for non-fasting blood glucose>300 mg/dL. M: indicates methylated plasmid DNA; 4:1:40 and 10 μg, respectively, of the indicated plasmid DNA constructs; 4:2, 40 and 20 μg, respectively, of the indicated plasmid DNA constructs; *: P<0.05 (Kaplan-Meier).

In two groups, the plasmids were administered as 4:1 (4:1 ratio of the plasmid DNAs). 60 micrograms of DNA vaccines consisting of 40 micrograms methylated plasmid DNA coding for secreted glutamic acid decarboxylase (mSGAD) and 20 micrograms plasmid DNA coding for pro-apoptotic protein BAX, where the DNA was either unmethylated (BAX) or methylated (mBAX). In another two groups, the plasmids were administered as 4:2 (4:2 ratio of the plasmid DNAs). * P<0.05, Kaplan Meyer. FIG. 2 shows that the vaccines containing lower levels of methylation had higher therapeutic efficacy (previous work showed that unmethylated DNA vaccines had no therapeutic efficacy).

Particularly interesting is that injection of 40 micrograms msGAD with 20 micrograms BAX (hypomethylated) significantly ameliorated disease. Unexpectedly, however, injection of 40 micrograms msGAD and 20 micrograms mBAX (hypermethylated) did not. Therefore, hypermethylation of both plasmid DNA constructs actually caused a decrease in T1D treatment efficacy.

Furthermore, analysis of immune responses induced by injection of sGAD with BAX (hypomethylated), msGAD with BAX (hypomethylated), and msGAD with mBAX (hypermethylated) provided additional information on the effects of DNA hypermethylation and supported the conclusion that a mix of hypomethylated and hypermethylated DNA is superior to hypomethylated or hypermethylated DNA alone for induction of a tolerogenic immune response.

Example 3

Demonstration of CD8+ Cell Penetration of Islet Cells In Vivo

Protocol: 10-week-old, 6 NOD/group, 3 NOD pooled, duplicated assay. Mice were treated as follows:
  Group 1. Vector pMDV alone, 70 ug i.d. for 2 weeks, 3 times;
  Group 2. SGAD+BAX=4:3, 70 ug i.d. for 2 weeks, 3 times; (no methylated plasmid DNA);
  Group 3. mSGAD+BAX=4:3, 70 ug i.d. for 2 weeks, 3 times; (40 ug plasmid DNA methylated); and
  Group 4. mSGAD+mBAX, 70 ug i.d. for 2 weeks, 3 times; (70 ug plasmid DNA methylated).

Islet Isolation & Culture

Isolation: Modified Pittsburgh protocol, all hand-picked, no Ficoll, 50-100 islets per NOD.

Culture: Islets were cultured in a 60 mm plate with T cell medium plus rhIL2 for 7 days (medium changed at day 4), islets were removed, and resuspended cells were collected by centrifugation.

FACS—Surface & Intracellular Staining: Collected cells were stained in 10% FCS-PBS on ice for 30 min. with anti-CD4-PE, anti-CD8-FITC, and anti-CD25-PECy5 Abs, and cells were washed. The Intracellular Cellular Staining Kit (eBioscience, San Diego), was used: briefly, cells were fixed in Fixation/Permeabilization Solution for 30 min., washed, and then anti-FoxP3-PECy5 or anti-IL17-PerCPCy5.5 plus Permeabilization Buffer was applied for the other 30 min., washed, and cells were measured in FACS buffer by Flow Cytometer (Becton Dickinson, San Jose). PI staining was used to confirm unfixed cells that cell viabilities were higher than 95%.

Figure 3:
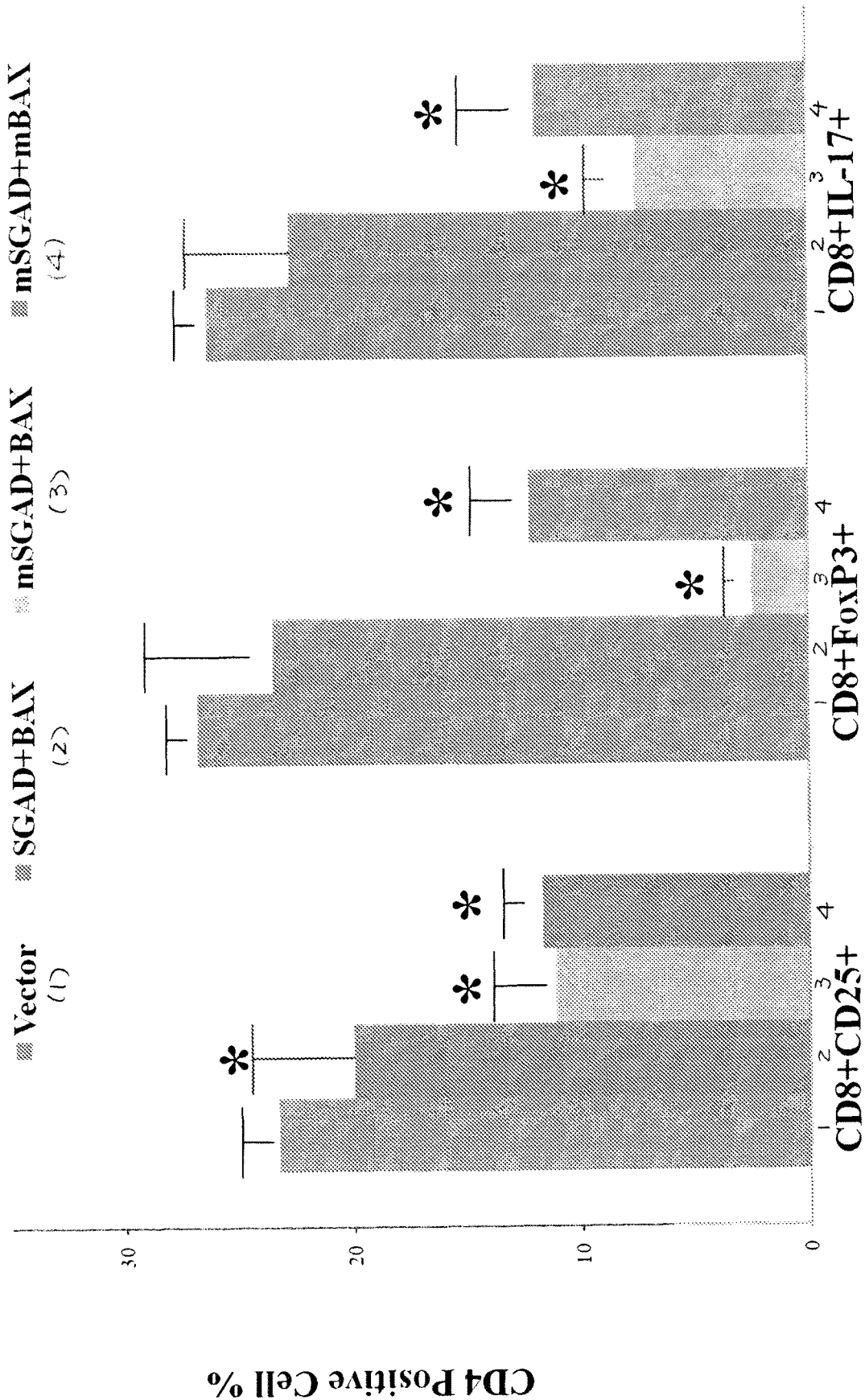
FIG. 3 shows the effects of DNA methylation levels on CD8+ T cells infiltration in pancreatic islets of immunized female non-obese diabetic (NOD) mice (Type 1 diabetes (T1D) model). Plasmid DNA was methylated using a DH5-alpha E. coli strain carrying a single copy of the sssI gene in its chromosome.

FIG. 3 shows the effects of DNA methylation levels on CD8+ T cells infiltration in pancreatic islets of immunized female NOD mice (T1D model). Plasmid DNA was methylated using a DH5-alpha *E. coli* strain carrying a single copy of the sssI gene in its chromosome. FIG. 3 further shows that increased DNA methylation causes decreased infiltration of islets by CD8+T lymphocytes.

Example 4

Demonstration of Increased Regulatory T-Cell (TREG) Phenotype In Vivo

Protocol: 8-week-old, 6 NOD/group, duplicated assay. Mice were treated as follows:
  Group 1. pMDV NM+M=4:3, 70 ug i.d. for 2 weeks, 3 times;
  Group 2. SGAD55+BAX=4:3, 70 ug i.d. for 2 weeks, 3 times;
  Group 3. mSGAD55+BAX=4:3, 70 ug i.d. for 2 weeks, 3 times; and
  Group 4. mSGAD55+mBAX=4:3, 70 ug i.d. for 2 weeks, 3 times.

LN & Spleen Isolation, Culture, & Separation

Axillary and pancreatic draining LN pooled, splenocytes were added to make up to 4×107 total cells in 8 ml medium. For each set: cells were loaded as 1 ml/well in a 24-well-plate for totally 8 wells, as 2 wells for No-Ag, 2 wells for Ins, and the last 2 wells for GAD Ag stimulation. Cells were cultured for 14 hrs with Ags plus CD154-PE Cocktail. Cells were collected and Anti-PE-bead were used to separate CD154+ cells (Protocol of Miltenyi, MN). CD154+ were cultured w/CD3CD28Beads+rhIL2 for 3 days. Cells were stained with appropriate antibodies for flow cytometric analysis.

Figure 4:
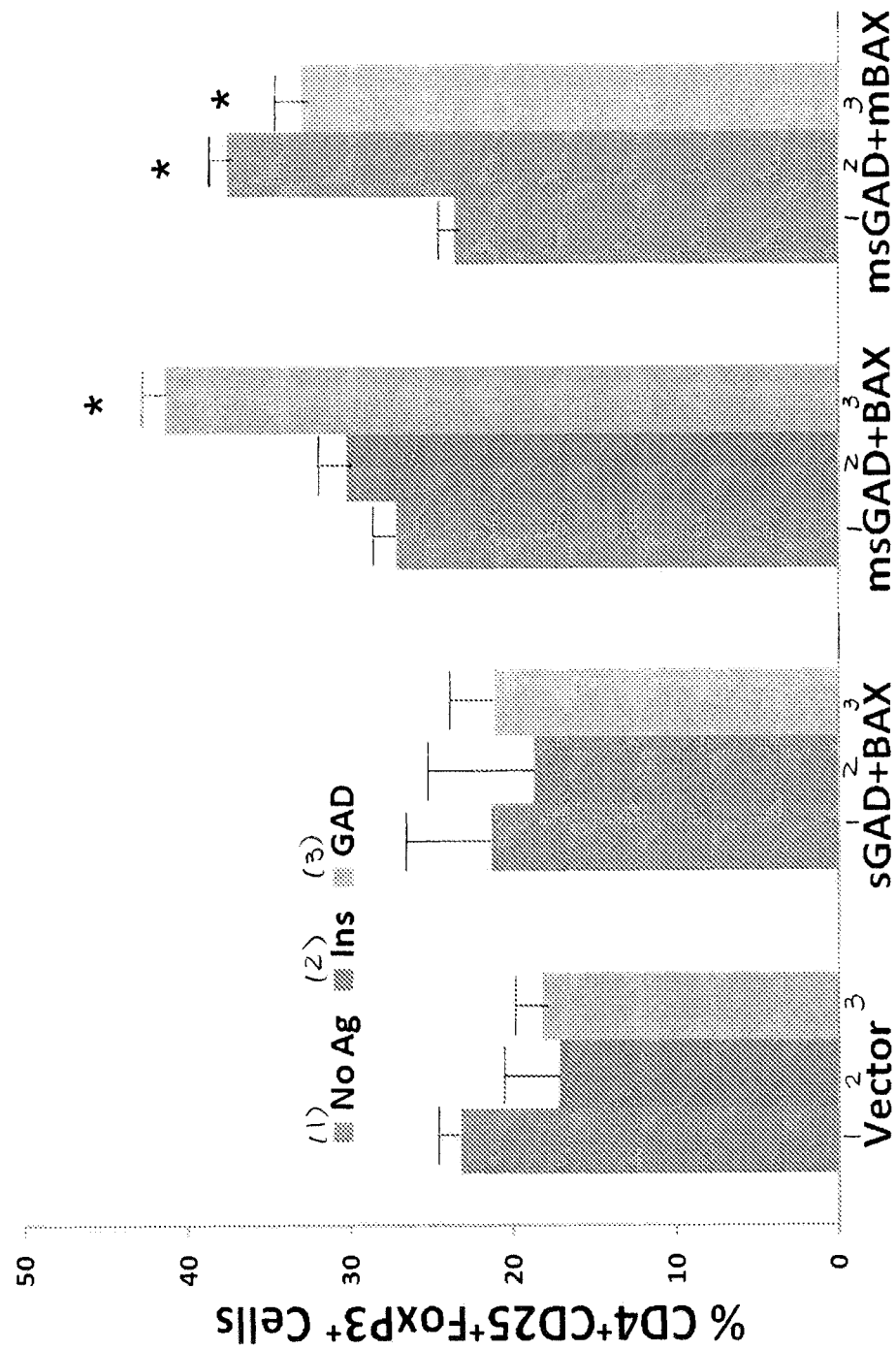
FIG. 4 shows the effects of DNA methylation levels in percent of cells with Tregulatory cell phenotype in lymph nodes of immunized female NOD mice (T1D model). Plasmid DNA was methylated with a DH5-alpha E. coli strain carrying a single copy of the sssI gene in its chromosome. The data in FIG. 4 show that increased DNA vaccine methylation causes an increased percent of cells with Treg phenotype. *, P<0.05.

FIG. 4 shows the effects of DNA methylation levels on the percentage of cells with Tregulatory cell phenotype in lymph nodes of immunized female NOD mice (T1D model). Plasmid DNA was methylated with a DH5-alpha *E. coli* strain carrying a single copy of the sssI gene in its chromosome. FIG. 4 further shows that increased DNA vaccine methylation causes an increased percentage of cells with Treg phenotype.

Example 5

Demonstration of Efficacy for Allograph Survival In Vivo

Protocol: C57/Bl6 mice (8-week-old) recipients (n=10/group) received BALB/c full-thickness skingrafts on their back at day 0;
  mice received Co60: Cobalt 3Gy at day 2, treated once;
  Rapamycin (Wyeth, Madison, NJ): 1 mg/kg BW daily until day 28; and
  plasmid DNA 50 ug i.d., 1 cm from graft at days 0, 3, 7, and then weekly.

Skin grafting was done as described in Li et al. 2010 *Vaccine* 28: 1897-1904. See, Li et al. 2010 and U.S. Pat. Pub. No. 2009/0191218 (Escher et al.) for additional experimental details.

Figure 5:
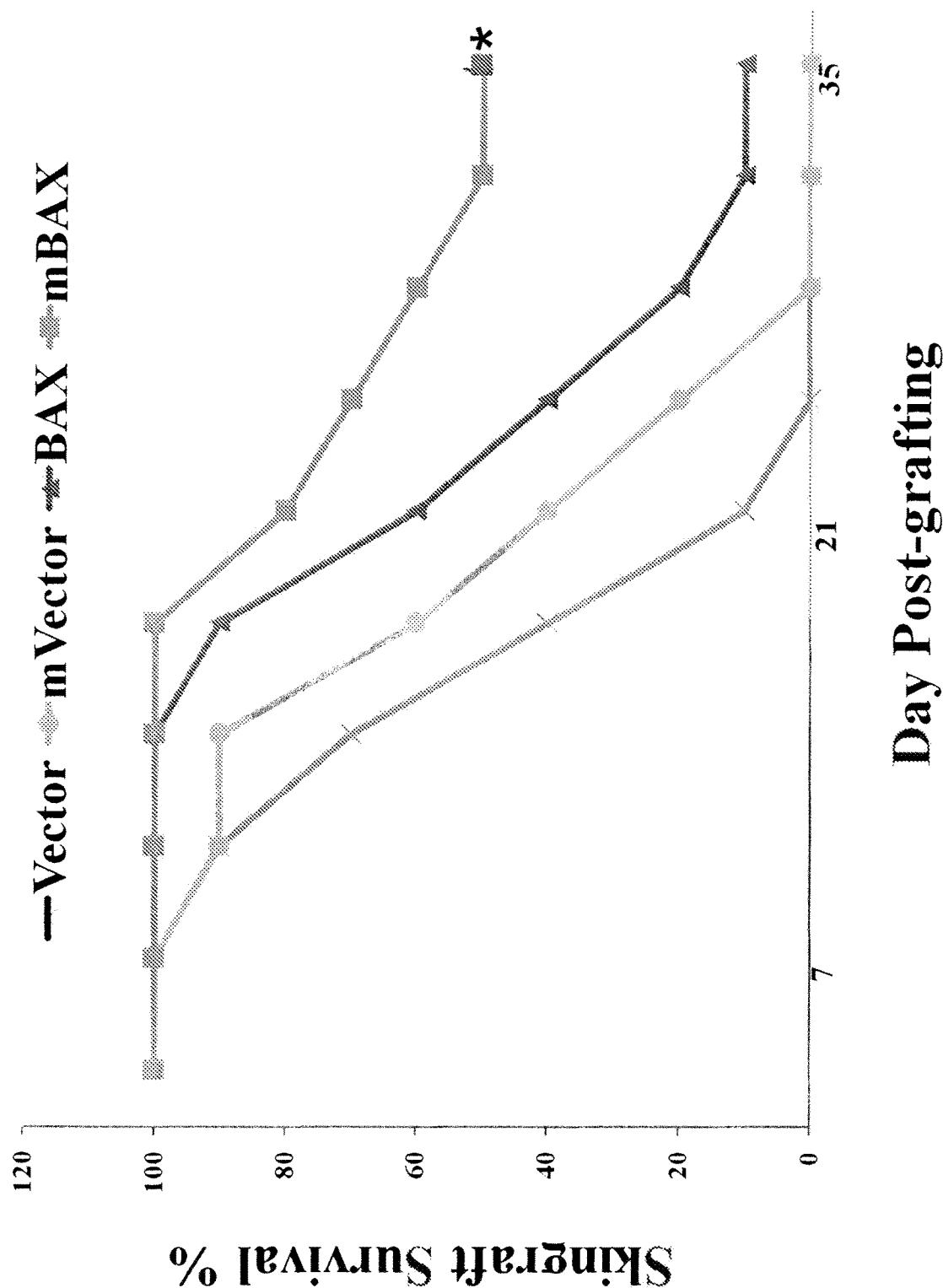
FIG. 5 shows the effect of CpG methylation of plasmid DNA on skin allograft survival. Plasmid DNA was methylated with a DH5-alpha E. coli strain carrying a single copy of the sssI gene in its chromosome. *, P<0.05, Kaplan Meyer. *, P<0.05.
Figure 6:
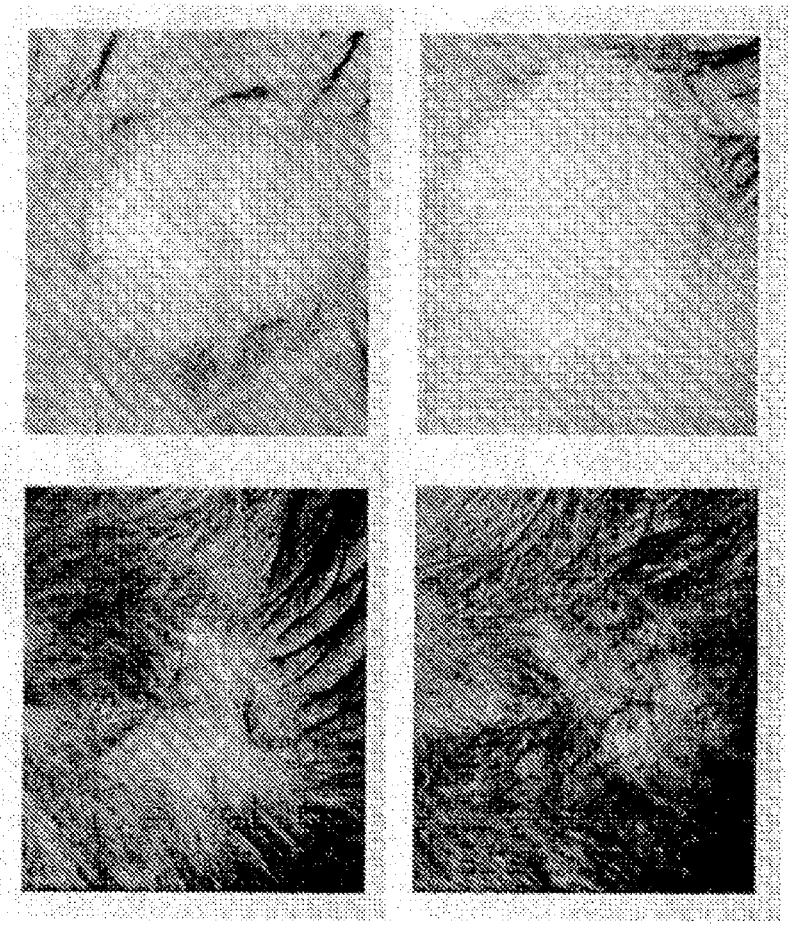
FIG. 6 illustrates the effect of DNA methylation on skin allografts. Only the methylated BAX DNA results in hair growth after 5 weeks.

FIG. 5 and FIG. 6 show the effect of CpG methylation of plasmid DNA on skin allograft survival. Plasmid DNA was methylated with a DH5-alpha *E. coli* strain carrying a single copy of the sssI gene in its chromosome. *, $P<0.05$, Kaplan Meyer.

Example 6

Modulating Plasmid DNA CPG-Methylation to Improve Tolerogenic Vaccination

Figure 7:
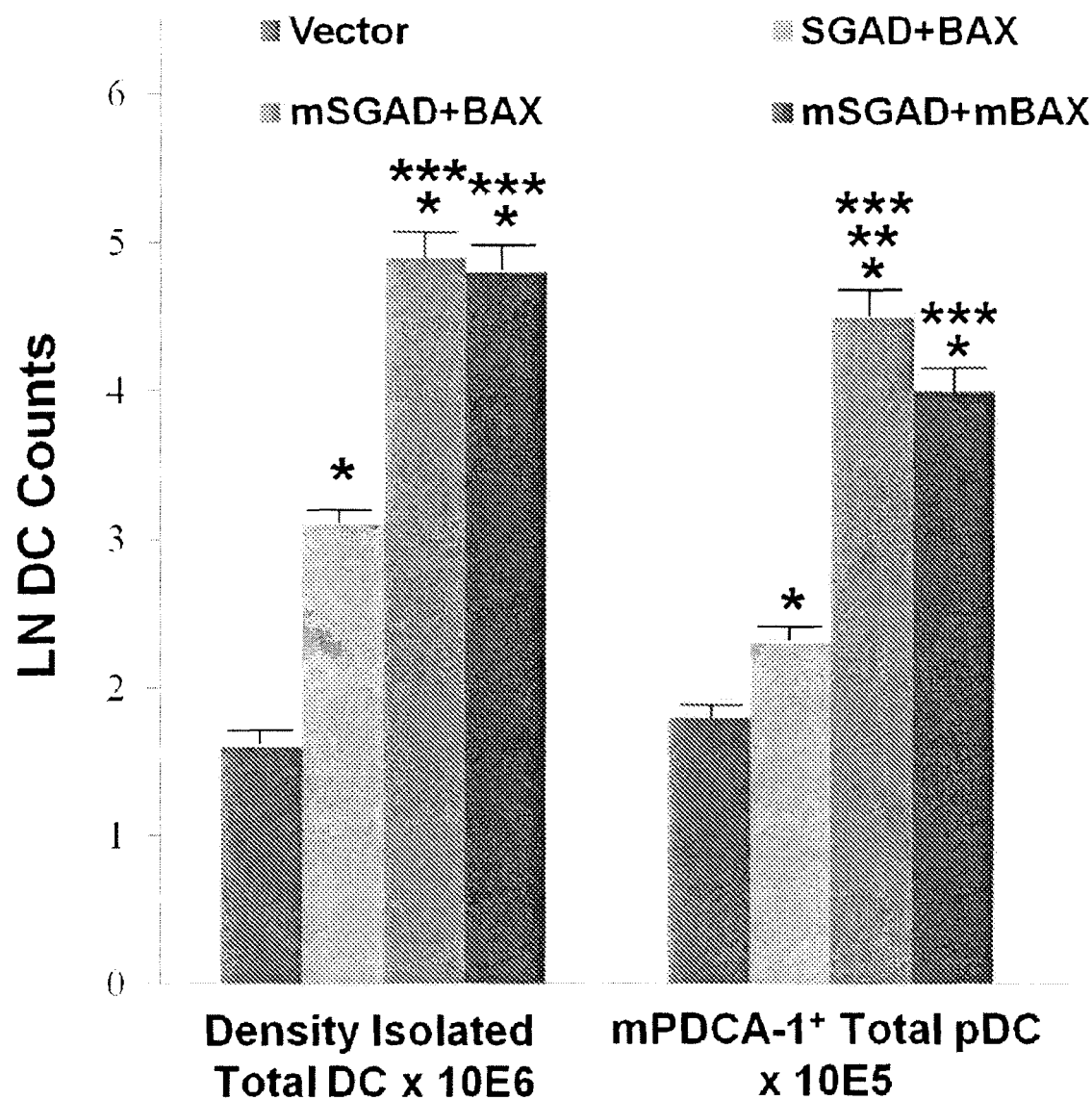
FIG. 7 shows that plasmid DNA hypermethylation causes increased recruitment of total DCs and pDCs. NOD mice (N=15/group) received i.d. injection of hypomethylated vector, hypomethylated (sGAD+BAX), partially hypermethylated (msGAD+BAX), or fully hypermethylated (msGAD+mBAX) plasmid DNA. Total DCs were isolated from pooled LNs using differential centrifugation, and counted (70-80% were CD11c+ as per flow cytometric analysis). A portion of total DCs was then used to isolate and count mPDCA-1+ pDCs using a MACs kit (Miltenyi Biotec, Auburn, CA). *, P<0.02 vs vector, , P<0.008 vs msGAD+mBAX, *, P<0.002 vs sGAD+BAX.

The experimental setup is the same as Example 2. FIG. 7 shows that injection of fully hypermethylated (msGAD+mBAX) or partially hypermethylated DNA (msGAD+BAX) coding for sGAD and BAX promoted increased recruitment of DCs, and of plasmacytoid DCs (pDCs) in particular. Moreover, data indicate that the partially hypermethylated DNA recruited highest numbers of pDCS. The results are significant because pDCs are associated with induction of tolerance and amelioration of diabetes in NOD mice and humans.

Figure 8:
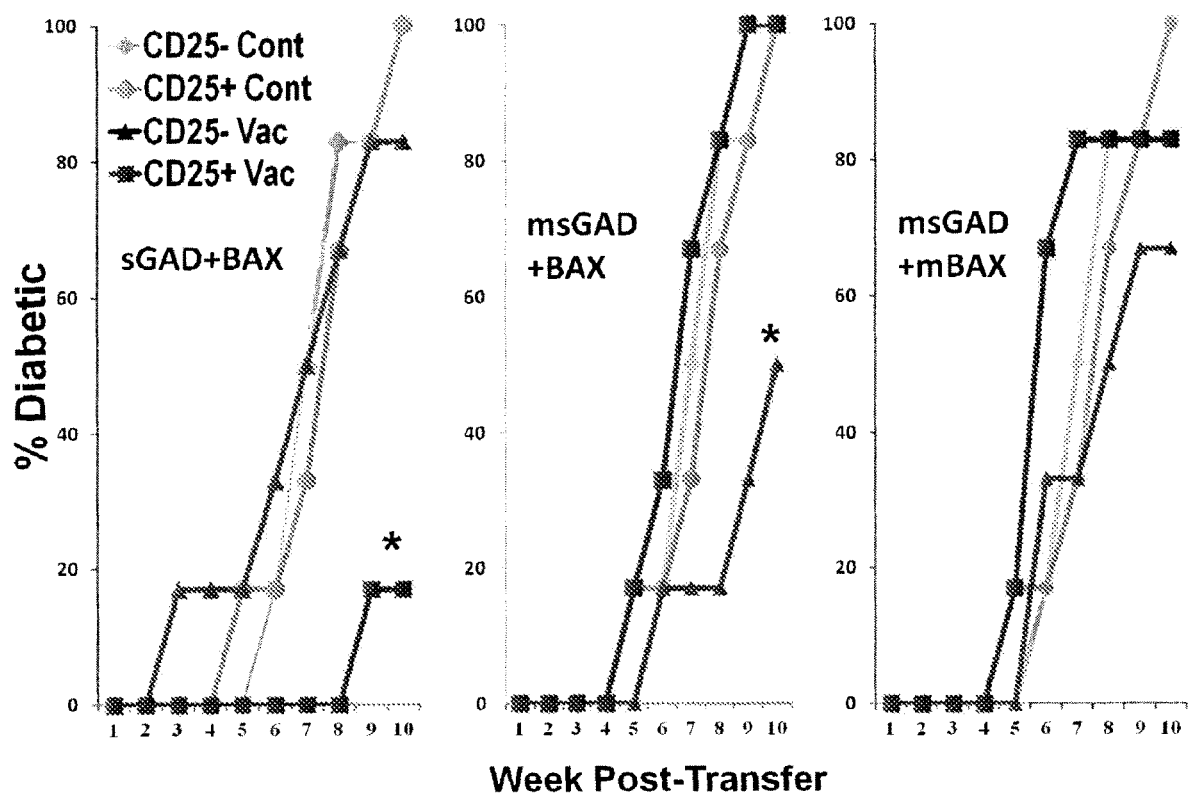
FIG. 8 shows that plasmid DNA hypermethylation affects Treg population and activity. CD4+CD25+ and CD4+CD25– T lymphocytes were isolated from spleen of NOD mice (N=6-8/group) immunized with the indicated DNA constructs (2:1 ratio) with increased levels of CpG methylation (m). Cells were then co-transferred i.v. with diabetogenic NOD T lymphocytes into NOD-scid mice (N=6/group) to investigate diabetes suppression and Treg activity. Contr, cells isolated from untreated mice, Vac, cells isolated from mice receiving the indicated DNA. *, P<0.05, Kaplan-Meier.

FIG. 8 shows that DNA hypermethylation causes a shift in regulatory T lymphocyte activity and that methylation levels modulate Treg function. Plasmid DNA hypermethylation has a significant impact on Tregs. The figure shows the effects of the same constructs described in FIG. 7, but this time on Treg activity in vivo after adoptive transfer of cells from spleen of treated NOD mice mixed with diabetogenic T cells and injected intravenously into NOD-scid mice which normally do not develop diabetes. Delayed diabetes in NOD-scid mice indicates suppressive activity of T cells from treated NOD mice acting on transferred diabetogenic T cells. Results indicated that the non-hypermethylated vaccine could induce $CD4^+CD25^+$ Tregs, although it does not ameliorate disease. Induction of Tregs in NOD mice without diabetes amelioration has been reported previously and suggests that Tregs may not be in sufficient numbers, specificity, and overall activity for the treatment to be effective in the vaccinated animal. Partial methylation of the DNA (msGAD+BAX or SKRS95) caused a shift in Treg population from CD4+CD25+ to CD4+CD25−. These splenic CD4+ CD25− cells may represent a population of adaptive Tregs because newly activated (CD154+) GAD-specific CD4+ CD25+FOXP3+ cells induced by GAD autoantigen were obtained from cultured LNs of NOD mice receiving SKRS95. The fact that Tregs transferred from SKRS95-treated NOD mice did not show increased amelioration of diabetes in NOD-scid compared to Tregs transferred from NODs receiving the non-hypermethylated DNA suggests that SKRS95 induces regulatory cell populations other than CD4+CD25−/CD25+ lymphocytes. With regard to the fully hypermethylated msGAD+mBAX DNA, it did not induce detectable splenic Treg activity in NOD-scid mice. Nonetheless, newly activated CD4+CD25+FOXP3+ cells could still be detected in cultured lymph nodes indicating that a certain level of Treg activity was induced after full DNA hypermethylation. Accordingly, partial methylation of the DNA (msGAD+BAX) caused a shift in Treg population from CD4+CD25+ to CD4+CD25−. The fully hypermethylated msGAD+mBAX DNA did not induce detectable splenic Treg activity in vivo.

Figure 9:
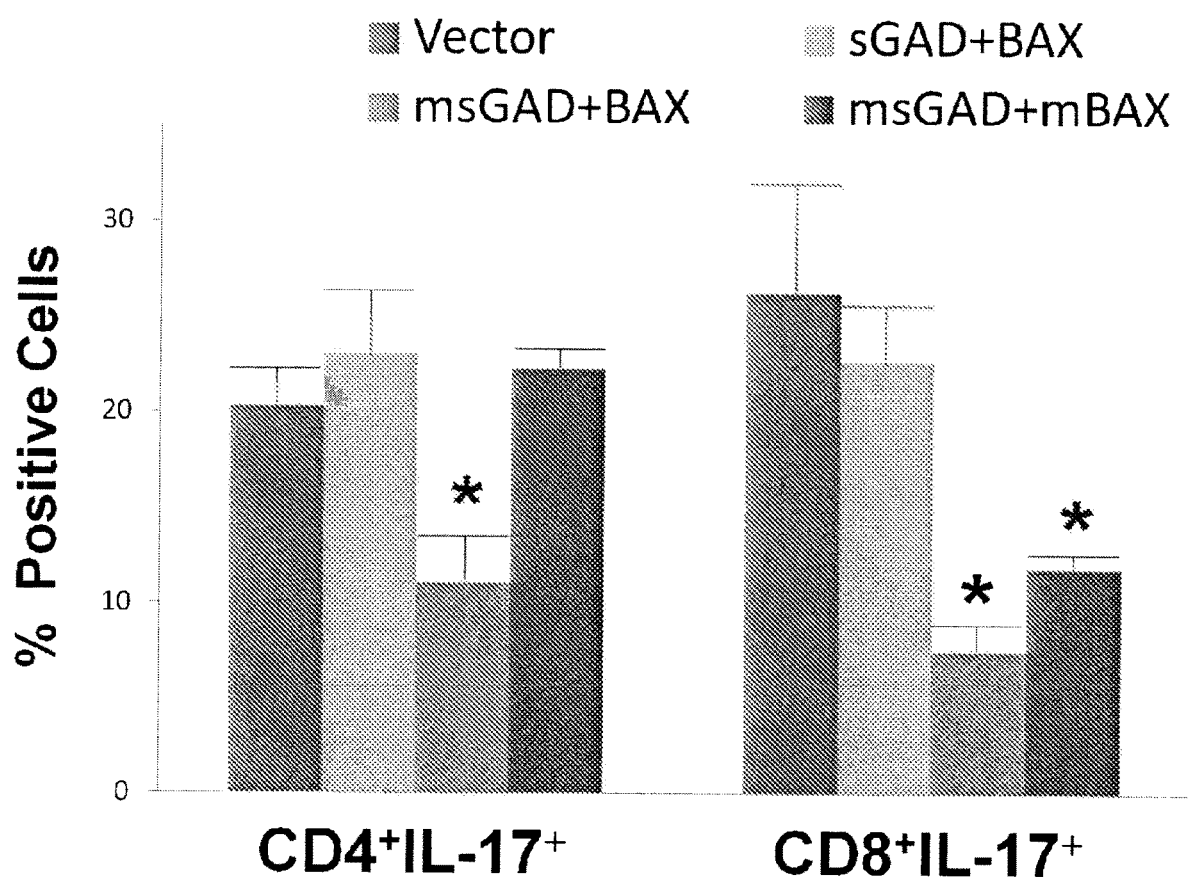
FIG. 9 shows that SKRS95 causes decreased percentage of both Th17 and Tc17 cells in cultured islets. Hand-picked islets were isolated from NOD mice receiving the indicated DNA (N=6/group, ~100 islets/mouse). Islets were cultured with IL-2 for 7 days, dispersed, and stained for CD4, CD8 and intracellular IL-17 with immunofuorescent mAbs for flow cytometric analysis. *, P<0.05.

FIG. 9 shows flow cytometric analysis of cells from cultured pancreatic islets of mice receiving the different plasmid DNA constructs. The data indicate that partially hypermethylated DNA was the only of the 4 tested DNAs (including control) that could cause a decrease in both CD4+IL17+ and CD8IL17+ cells which are also known as, respectively, Th17 and Tc17 cells. An increasing body of evidence implicates Th17 lymphocytes in the pathogenesis of T1D in NOD mice, and downregulation of these cells is associated with disease amelioration. As for Tc17 cells, they are a subgroup of CD8+ effector cells thought to have a pathogenic role in human autoimmune diseases like psoriasis, systemic lupus erythematosus, and immune thrombocytopenia. Furthermore, Tc17 cells have been shown to be diabetogenic in a RIP-mOVA mouse model of T1D. Therefore, our finding that msGAD with BAX cause a significant reduction in percentage of both Th17 and Tc17 in cultured islets is significant.

Together, FIGS. 2 and 7-9 support the conclusion that partial, but not complete, hypermethylation of plasmid DNA coding for sGAD and BAX promotes tolerogenic immune responses and treats diabetes successfully.

As mentioned previously, unmethylated CpG dinucleotides bind to the TLR9 receptor which then signals the presence of bacterial DNA to the mammalian host and promotes an inflammatory response. Accordingly, we investigated the role played by TLR9 in immune responses induced by msGAD+BAX plasmid DNA.

Figure 10:
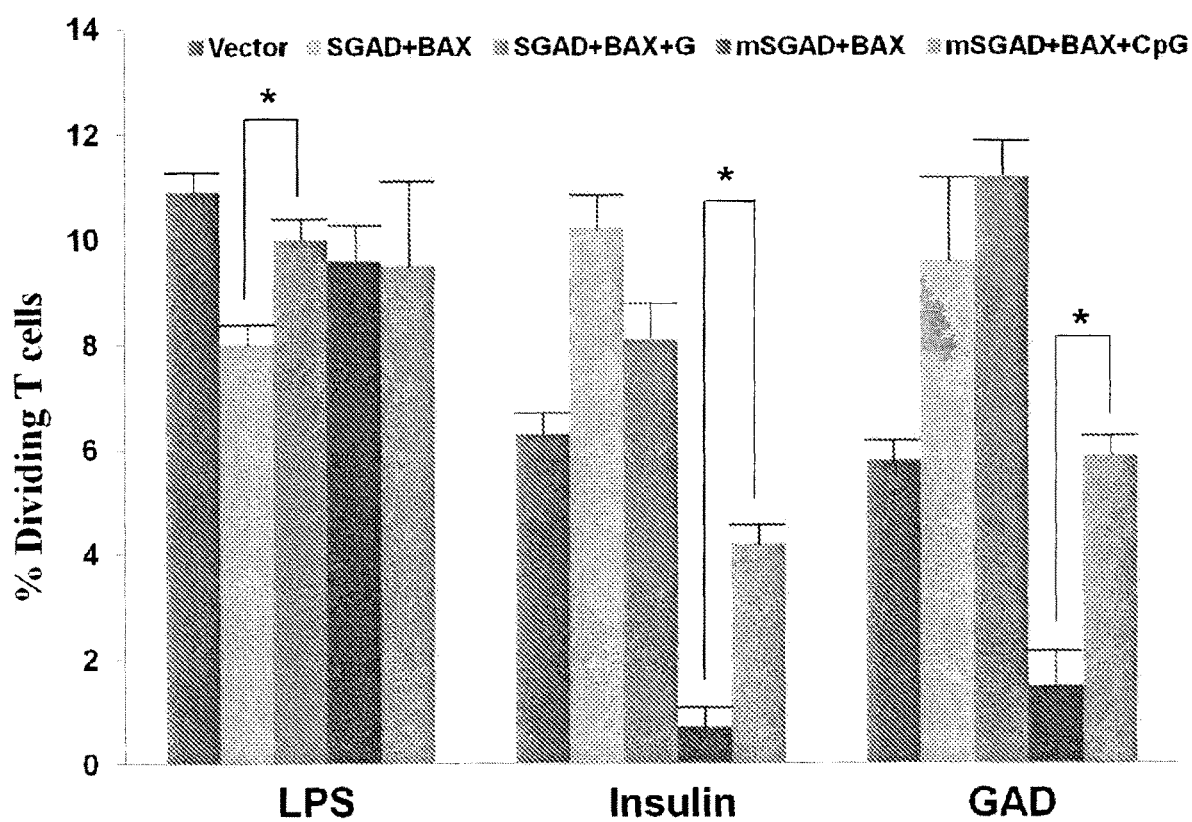
FIG. 10 shows that co-injection of CpG oligonucleotide causes a decrease in suppressive activity of pDCs induced by mSGAD+BAX DNA. 7-week-old female NOD mice (N=15/group), received 60 micrograms of the indicated DNA intradermally, i.e., hypomethylated sGAD+BAX DNA (2:1) or partially hypermethylated msGAD+BAX DNA (2:1) and 20 micrograms of oligonucleotide inhibiting binding of unmethylated CpG DNA to TLR9 (G), or 20 micrograms of CpG oligonucleotide binding to TLR9 (CpG) 3 times over 2 weeks. Axillary and pancreatic draining LN were pooled from 15 mice/group, and spleens were pooled from 4 untreated mice. LN DCs were pre-enriched using density centrifugations and LN pDCs were isolated using a pDC kit (Miltenyi, Auburn, CA). Untreated spleen Pan T cells were isolated using a Pan-T negative kit and stained with 1.5 μM CFSE. For each set cells were loaded as 100 ul DC+100 ul TC/well in 96-well-plates for totally 3 wells/Ag, 3 wells for LPS, 3 wells for Ins, and the last 3 wells for GAD antigen stimulation. Cells were cultured for 3 days with hrIL2. Cells were then collected and FACS was performed for CFSE+CD4+SYTOX– cells. pDC or cDC from vaccinated NOD and CFSE labeled (1.5 uM) Pan T cells from untreated NOD were added as 1:1 onto 96-well plate with IL-2 20 U/ml, and LPS 5 ug/ml, or Ins 20 ug/ml, or GAD 20 ug/ml as antigen stimulation, or without antigen. Cells were cultured in complete medium in a CO2 incubator for 3 days, and anti-CD4-PE Abs and Sytox were used to detect CFSE+CD4+Sytox– cell proliferations. FlowJo 7.6.5 software was used to analyze the proliferation data, and % Divided was used to represent differences between groups

FIG. 10 shows that co-injecting a CpG oligonucleotide that binds to TLR9 together with mSGAD+BAX DNA caused a decrease in the in vitro suppressive activity of pDCs isolated from treated NOD mice. These data suggest that further activation of TLR9 by the CpG oligonucleotide was detrimental to tolerogenic-like immune responses induced by the partially methylated plasmid DNA. Nevertheless, our previous data also clearly indicate that a certain level of unmethylated CpGs is necessary for therapeutic efficacy.

The unexpected finding that a certain level of unmethylated CpG dinucleotides is required to induce tolerogenic immune responses and successfully treat an inflammatory disorder like T1D has significant implications for the bench-to-bedside translation of our technology, because overall levels of TLR9 expression are known to be significantly different between mice and humans. Therefore, CpG-methylation levels will likely have to be adjusted for humans and presumably other species to optimize efficacy of treatment for a given disease in a given species. Furthermore, CpG-methylation levels may also have to be adjusted for a given individual within a species in the context of a specific disease. For example, kidney tissues from humans with lupus nephritis show higher levels of TLR9 compared with healthy individuals. Modulating level of unmethylated CpG dinucleotides for improved efficacy of immunotherapy would represent a novel means of personalized medicine for the treatment of inflammatory disorders.

REFERENCES

Klinman D M, Yamshchikov G, Ishigatsubo Y. Contribution of CpG motifs to the immunogenicity of DNA vaccines. J Immunol. 1997 Apr. 15; 158(8):3635-9.

Reyes-Sandoval A, Ertl H C. CpG methylation of a plasmid vector results in extended transgene product expression by circumventing induction of immune responses. Mol Ther. 2004 February; 9(2):249-61.

Ferguson T A, Choi J, Green D R. Armed response: how dying cells influence T-cell functions. Immunol Rev. 2011 May; 241(1):77-88.

Li A, Ojogho O, Franco E, Baron P, Iwaki Y, Escher A. Pro-apoptotic DNA vaccination ameliorates new onset of autoimmune diabetes in NOD mice and induces foxp3+ regulatory T cells in vitro. Vaccine. 2006 Jun. 5; 24(23): 5036-46.

Li A, Chen J, Hattori M, Franco E, Zuppan C, Ojogho O, Iwaki Y, Escher A. A therapeutic DNA vaccination strategy for autoimmunity and transplantation. Vaccine. 2010 Feb. 23; 28(8):1897-904.

Saxena V, Ondr J K, Magnusen A F, Munn D H, Katz J D. The countervailing actions of myeloid and plasmacytoid dendritic cells control autoimmune diabetes in the nonobese diabetic mouse. J Immunol. 2007 Oct. 15; 179(8): 5041-53.

Nikolic T, Welzen-Coppens J M, Leenen P J, Drexhage H A, Versnel M A. Plasmacytoid dendritic cells in autoimmune diabetes—potential tools for immunotherapy. Immunobiology. 2009; 214(9-10):791-9.

Every A L, Kramer D R, Mannering S I, Lew A M, Harrison L C. Intranasal vaccination with proinsulin DNA induces regulatory CD4+ T cells that prevent experimental autoimmune diabetes. J Immunol. 2006 Apr. 15; 176(8):4608-15.

Jain R, Tartar D M, Gregg R K, Divekar R D, Bell J J, Lee H H, Yu P, Ellis J S, Hoeman C M, Franklin C L, Zaghouani H. Innocuous IFNgamma induced by adjuvant-free antigen restores normoglycemia in NOD mice through inhibition of IL-17 production. J Exp Med. 2008 Jan. 21; 205(1):207-18.

Emamaullee J A, Davis J, Merani S, Toso C, Elliott J F, Thiesen A, Shapiro A M. Inhibition of Th17 cells regulates autoimmune diabetes in NOD mice. Diabetes. 2009 June; 58(6):1302-11.

Bertin-Maghit S, Pang D, O'Sullivan B, Best S, Duggan E, Paul S, Thomas H, Kay T W, Harrison L C, Steptoe R, Thomas R. Interleukin-1β produced in response to islet autoantigen presentation differentiates T-helper 17 cells at the expense of regulatory T-cells: Implications for the timing of tolerizing immunotherapy. Diabetes. 2011 January; 60(1):248-57.

Zhang J, Huang Z, Sun R, Tian Z, Wei H. IFN-γ induced by IL-12 administration prevents diabetes by inhibiting pathogenic IL-17 production in NOD mice. J Autoimmun. 2012 February; 38(1):20-8.

Res P C, Piskin G, de Boer O J, van der Loos C M, Teeling P, Bos J D, Teunissen M B. Overrepresentation of IL-17A and IL-22 producing CD8 T cells in lesional skin suggests their involvement in the pathogenesis of psoriasis. PLoS One. 2010 Nov. 24; 5(11):e14108.

Henriques A, Inês L, Couto M, Pedreiro S, Santos C, Magalhães M, Santos P, Velada I, Almeida A, Carvalheiro T, Laranjeira P, Morgado J M, Pais M L, da Silva J A, Paiva A. Frequency and functional activity of Th17, Tc17 and other T-cell subsets in Systemic Lupus Erythematosus. Cell Immunol. 2010; 264(1):97-103.

Hu Y, Ma D X, Shan N N, Zhu Y Y, Liu X G, Zhang L, Yu S, Ji C Y, Hou M. Increased number of Tc17 and correlation with Th17 cells in patients with immune thrombocytopenia. PLoS One. 2011; 6(10):e26522.

Ciric B, El-behi M, Cabrera R, Zhang G X, Rostami A. IL-23 drives pathogenic IL-17-producing CD8+ T cells. J Immunol. 2009 May 1; 182(9):5296-305.

Mestas J, Hughes C C. Of mice and not men: differences between mouse and human immunology. J Immunol. 2004 Mar. 1; 172(5):2731-8.

Campbell J D, Cho Y, Foster M L, Kanzler H, Kachura M A, Lum J A, Ratcliffe M J, Sathe A, Leishman A J, Bahl A, McHale M, Coffman R L, Hessel E M. CpG-containing immunostimulatory DNA sequences elicit TNF-alpha-dependent toxicity in rodents but not in humans. J Clin Invest. 2009 September; 119(9):2564-76.

It is to be understood that, while the subject technology has been described in conjunction with the detailed description, thereof, the foregoing description is intended to illustrate and not limit the scope of the subject technology. Other aspects, advantages, and modifications of the subject technology are within the scope of the claims set forth below. The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patents, and sequences cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

What is claimed is:

1. A composition comprising:
   a first methylated polynucleotide encoding a pro-apoptotic protein and having a CpG methylation level of about 15% or less; and
   a second methylated polynucleotide encoding an antigen and having a CpG methylation level of about 25%;
   for use in the induction of a tolerogenic immune response against the antigen.

2. The composition of claim 1, wherein the ratio of the first methylated polynucleotide to the second methylated polynucleotide in the composition ranges from about 1:5 to about 1:1 (μg:μg).

3. The composition of claim 2, wherein the ratio of the first methylated polynucleotide to the second methylated polynucleotide in the composition is about 1:2 (μg:μg).

4. The composition of claim 1, wherein the composition further comprises a pharmaceutically acceptable carrier.

5. The composition of claim 1, wherein the pro-apoptotic protein is BAX, BAK, BIM, Death Receptor 4 (DR4), Death Receptor 5 (DR5), a FAS receptor, or a functional pro-apoptotic fragment thereof.

6. The composition of claim 5, wherein the pro-apoptotic protein is BAX or a functional pro-apoptotic fragment thereof.

7. The composition of claim 1, wherein the antigen is associated with an autoimmune disease.

8. The composition of claim 7, wherein the autoimmune disease is selected from the group consisting of autoimmune hepatitis, vitiligo, diabetes mellitus type 1, Addison's disease, Grave's disease, Hashimoto's thyroiditis, multiple sclerosis, polymyalgia rheumatic, Reiter's syndrome, Crohn's disease, Goodpasture's syndrome, Gullain-Barre syndrome, lupus nephritis, rheumatoid arthritis, systemic lupus erythematosus, Wegener's granulomatosis, celiac disease, dermatomyositis, eosinophilic fasciitis, idiopathic thrombocytopenia purpura, Miller-Fisher syndrome, myasthenia gravis, pemphigus vulgaris, pernicious anaemia, polymyositis, primary biliary cirrhosis, psoriasis, psoriatic arthritis, rheumatoid arthritis, and Sjogren's syndrome.

9. The composition of claim 1, wherein the antigen is associated with one of an immune-mediated inflammatory disorder or an allergy.

10. The composition of claim 9, wherein the immune-mediated inflammatory disorder is solid organ transplant rejection, graft versus host disease, or host versus graft disease, or wherein the allergy is a peanut allergy, a pollen allergy, or a cat allergy.

11. The composition of claim 1, wherein the antigen is glutamic acid decarboxylase (GAD), a secreted form of GAD (sGAD), or an antigenic fragment thereof.

12. The composition of claim 1, wherein the antigen is carbonic anhydrase II, chromogranin, cytochrome P450 family 2 subfamily device 400 polypeptide 6 (CYP2D6), hCDR1, HSP60, IGRP, insulin, myelin basic protein, hNinein, Ro 60 kDa, SRY-box containing gene 10 (SOX-IO), ZnT8, proteolipid protein PLP-1, myelin associated oligodendrocytic basic protein, myelin associated glycoprotein, alpha-B-crystallin, cyclic nucleotide phosphodiesterase, myelin oligodendrocyte glycoprotein, pre-proinsulin, proinsulin, tyrosine phosphatase IA2, carboxypeptidase H, glima 38, islet cell antigen 69 kDa, P52, islet cell glucose transporter GLUT-2, peripheral myelin protein I, cholinergic receptor a-chain, thyoglobulin, thyroid peroxidase, type I, II, III, IV, V, IX, or XI collagen, immunoglobulin, fibrin, filaggrin, GP39, hnRNP, matrix mettaloproteinase MMP-1, S-antigen, interphotoreceptor retinoid binding protein (IRBP), rhodopsin, recoverin, pyruvate dehydrogenase complex, 2-oxoacid dehydrogenase, a liver hepatocyte antigen, desmoglein-1, desmogelin-3, H+/K+ ATPase, intrinsic factor, histidyl tRNA synthetase, thyroid-stimulating hormone receptor, tyrosinase, tyrosinase-related protein 2, a systemic nuclear antigen, DNA, histone, ribonucleoprotein, or transglutaminase, or an antigenic fragment thereof.

13. The composition of claim 1, wherein the antigen is peanut allergen Ara h 1, 2, 3; pollen allergen Phl p 1, 2, 5a, 5b, 6, Bet v 1; cat allergen Fel d 1, or an antigenic fragment thereof.

14. The composition of claim 1, wherein the ratio of the first and second polynucleotides results in a total CpG methylation level of at least about 25%.

15. A composition comprising:
   a first methylated plasmid DNA encoding a pro-apoptotic protein and having a CpG methylation level of about 15% or less; and
   a second methylated plasmid DNA encoding an antigen and having a CpG methylation level of about 25%;
   for use in the induction of a tolerogenic immune response against the antigen.

16. The composition of claim 15, wherein the ratio of the first methylated plasmid DNA to the second methylated plasmid DNA in the composition ranges from about 1:5 to about 1:1 (µg:µg).

17. The composition of claim 16, wherein the ratio of the first methylated plasmid DNA to the second methylated plasmid DNA in the composition is about 1:2 (µg:µg).

18. The composition of claim 15, wherein the pro-apoptotic protein is BAX, BAK, BIM, Death Receptor 4 (DR4), Death Receptor 5 (DR5), a FAS receptor, or a functional pro-apoptotic fragment thereof.

* * * * *

SEQUENCE LISTING

```
<160> NUMBER OF SEQ ID NOS: 4

<210> SEQ ID NO 1
<211> LENGTH: 1868
<212> TYPE: DNA
<213> ORGANISM: Homo sapiens

<400> SEQUENCE: 1
gagctccacc gcggtggcgg ccgctctaga ccaccatggc atctccgggc tctggctttt      60
ggtctttcgg gtcggaagat ggctctgggg attccgagaa tcccggcaca gcgcgagcct     120
ggtgccaagt ggctcagaag ttcacgggcg gcatcggaaa caaactgtgc gccctgctct     180
acggagacgc cgagaagccg gcggagagcg gcgggagcca accccgcgg gccgccgccc      240 ggaaggccgc ctgcgcctgc gaccagaagc cctgcagctg ctccaaagtg gatgtcaact     300
acgcgtttct ccatgcaaca gacctgctgc cggcgtgtga tggagaaagg cccactttgg     360
cgtttctgca agatgttatg aacatttac ttcagtatgt ggtgaaaagt ttcgatagat       420
caaccaaagt gattgatttc cattatccta atgagcttct ccaagaatat aattgggaat     480 tgcagacca accacaaaat ttggaggaaa ttttgatgca ttgccaaaca actctaaaat      540
atgcaattaa aacagggcat cctagatact tcaatcaact ttctactggt ttggatatgg     600
ttggattagc agcagactgg ctgacatcaa cagcaaatac taacatgttc acctatgaaa     660
ttgctccagt atttgtgctt ttggaatatg tcacactaaa gaaaatgaga gaaatcattg     720
gctggccagg gggctctggc gatgggatat tttctcccgg tggcgccata tctaacatgt     780
atgccatgat gatcgcacgc tttaagatgt tcccagaagt caaggagaaa ggaatggctg     840
ctcttcccag gctcattgcc ttcacgtctg aacatagtca ttttctctc aagaagggag      900 ctgcagcctt agggattgga agagacagcg tgattctgat taatgtgat gagagaggga      960 aaatgattcc atctgatctt gaaagaagga ttcttgaagc caaacagaaa gggtttgttc    1020
```

```
ctttcctcgt gagtgccaca gctggaacca ccgtgtacgg agcatttgac cccctcttag    1080
ctgtcgctga catttgcaaa aagtataaga tctggatgca tgtggatgca gcttggggtg    1140
ggggattact gatgtcccga aaacacaagt ggaaactgag tggcgtggag agggccaact    1200
ctgtgacgtg aatccacac aagatgatgg gagtcccttt gcagtggtct gctctcctgg     1260
ttagagaaga gggattgatg cagaattgca accaaatgca tgcctcctac ctctttcagc    1320
aagataaaca ttatgacctg tcctatgaca ctggagacaa ggccttacag tgcggacgcc    1380
acgttgatgt ttttaaacta tggctgatgt ggagggcaaa ggggactacc gggtttgaag    1440
cgcatgttga taaatgtttg gagttggcag agtatttata caacatcata aaaaaccgag    1500
aaggatatga gatggtgttt gatgggaagc tgaggacac aaatgtctgc ttctggtaca     1560
ttcctccaag cttgcgtact ctggaagaca tgaagagag aatgagtcgc ctctcgaagg     1620
tggctccagt gattaaagcc agaatgatgg agtatggaac cacaatggtc agctaccaac    1680
ccttgggaga caaggtcaat ttcttccgca tggtcatctc aaacccagcg gcaactcacc    1740
aagacattga cttcctgatt gaagaaatag aacgccttgg acaagattta taataacctt    1800
gctcaccaag ctgttccact tctctaggta gcgacctcga gcggccgctc gagggggggc    1860
ccggtacc                                                            1868

<210> SEQ ID NO 2
<211> LENGTH: 1638
<212> TYPE: DNA
<213> ORGANISM: Artificial Sequence
<220> FEATURE:
<223> OTHER INFORMATION: Description of Artificial Sequence: Synthetic
      secreted form of human GAD

<400> SEQUENCE: 2
atgtacagga tgcaactcct gtcttgcatt gcactaagtc ttgcacttgt cacaaacagt      60
gcacctactt acgcgtttct ccatgcaaca gacctgctgc cggcgtgtga tggagaaagg    120
cccactttgg cgtttctgca agatgttatg aacatttac ttcagtatgt ggtgaaaagt     180
ttcgatagat caaccaaagt gattgattc cattatccta atgagcttct ccaagaatat     240
aattgggaat ggcagaccca accacaaaat ttggaggaaa ttttgatgca ttgccaaaca    300
actctaaaat atgcaattaa acagggcat cctagatact tcaatcaact ttctactggt     360
ttggatatgg ttgattagc agcagactgg ctgacatcaa cagcaaatac taacatgttc     420
acctatgaaa ttgctccagt atttgtgctt ttggaatatg tcacactaaa gaaaatgaga    480
gaaatcattg gctggccagg gggctctggc gatgggatat tttctcccgg tggcgccata    540
tctaacatgt atgccatgat gatcgcacgc tttaagatgt tcccagaagt caaggagaaa    600
ggaatggctg ctcttcccag gctcattgcc ttcacgtctg aacatagtca ttttctctc      660 aagaagggag ctgcagcctt agggattgga agagacagcg tgattctgat taaatgtgat    720
gagagaggga aatgattcc atctgatctt gaaagaagga ttcttgaagc caaacagaaa     780
gggtttgttc cttttcctcgt gagtgccaca gctggaacca ccgtgtacgg agcatttgac    840
cccctcttag ctgtcgctga catttgcaaa aagtataaga tctggatgca tgtggatgca    900
gcttggggtg ggggattact gatgtcccga aaacacaagt ggaaactgag tggcgtggag    960
agggccaact ctgtgacgtg aatccacac aagatgatgg gagtcccttt gcagtggtct    1020
gctctcctgg ttagagaaga gggattgatg cagaattgca accaaatgca tgcctcctac    1080
ctctttcagc aagataaaca ttatgacctg tcctatgaca ctggagacaa ggccttacag    1140
```

```
tgcggacgcc acgttgatgt ttttaaacta tggctgatgt ggagggcaaa ggggactacc    1200
gggtttgaag cgcatgttga taaatgtttg gagttggcag agtatttata caacatcata    1260
aaaaaccgag aaggatatga gatggtgttt gatgggaagc ctgaggacac aaatgtctgc    1320
ttctggtaca ttcctccaag cttgcgtact ctggaagaca atgaagagag aatgagtcgc    1380
ctctcgaagg tggctccagt gattaaagcc agaatgatgg agtatggaac cacaatggtc    1440
agctaccaac ccttgggaga caaggtcaat ttcttccgca tggtcatctc aaacccagcg    1500
gcaactcacc aagacattga cttcctgatt gaagaaatag aacgccttgg acaagattta    1560
taataacctt gctcaccaag ctgttccact tctctaggta gcgacctcga gcggccgctc    1620
gagggggggc ccggtacc                                                  1638

<210> SEQ ID NO 3
<211> LENGTH: 579
<212> TYPE: DNA
<213> ORGANISM: Homo sapiens

<400> SEQUENCE: 3
atggacgggt ccggggagca gcccagaggc gggggggccca ccagctctga gcagatcatg     60
aagacagggg ccctttttgct tcagggtttc atccaggatc gagcagggcg aatgggggg    120 gaggcacccg agctggccct ggacccggtg cctcaggatg cgtccaccaa gaagctgagc    180
gagtgtctca agcgcatcgg ggacgaactg gacagtaaca tggagctgca gaggatgatt    240
gccgccgtgg acacagactc cccccgagag gtcttttttcc gagtggcagc tgacatgttt    300
tctgacggca acttcaactg gggccgggtt gtcgcccttt tctactttgc cagcaaactg    360
gtgctcaagg ccctgtgcac caaggtgccg gaactgatca gaaccatcat gggctggaca    420
ttggacttcc tccgggagcg gctgttgggc tggatccaag accagggtgg ttgggacggc    480
ctcctctcct actttgggac gcccacgtgg cagaccgtga ccatctttgt ggcgggagtg    540
ctcaccgcct cgctcaccat ctggaagaag atgggctga                           579

<210> SEQ ID NO 4
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggatccgcgt aatcatcggc tcgtataatg tgtgaattgt gagcggataa caatttcaca     60
caggaaacag acc                                                       73
```